United States Patent [19]

Lewis et al.

[11] Patent Number: 5,461,146
[45] Date of Patent: Oct. 24, 1995

[54] SELECTED PROTEIN KINASE INHIBITORS FOR THE TREATMENT OF NEUROLOGICAL DISORDERS

[75] Inventors: Michael E. Lewis, West Chester; James C. Kauer, Kennett Square; Nicola Neff, Wallingford; Jill Roberts-Lewis, West Chester, all of Pa.; Chikara Murakata, Hachioji, Japan; Hiromitsu Saito, Mishima, Japan; Yuzuru Matsuda, Koganei, Japan; Marcie A. Glicksman, Swarthmore, Pa.

[73] Assignees: Cephalon, Inc., West Chester, Pa.; Kyowa Hakko Kogyo Co., Ltd., Tokyo, Japan

[21] Appl. No.: 96,561

[22] Filed: Jul. 22, 1993

Related U.S. Application Data

[63] Continuation-in-part of Ser. No. 920,102, Jul. 24, 1992, abandoned.

[51] Int. Cl.⁶ .......................... C07D 498/22; A61K 31/55
[52] U.S. Cl. .......................... 540/545; 548/416; 514/211; 514/279
[58] Field of Search .......................... 540/545; 514/211

[56] References Cited

U.S. PATENT DOCUMENTS

| | | | |
|---|---|---|---|
| 4,554,402 | 11/1985 | Hawkins et al. | 174/42 |
| 4,735,939 | 4/1988 | McCoy et al. | 514/211 |
| 4,816,450 | 3/1989 | Bell et al. | 514/25 |
| 4,877,776 | 10/1989 | Murakata et al. | 514/43 |
| 4,923,986 | 5/1990 | Murakata et al. | 540/545 |
| 5,093,330 | 3/1992 | Caravatti et al. | 540/545 |

FOREIGN PATENT DOCUMENTS

| | | |
|---|---|---|
| 17571/88 | 12/1988 | Australia. |
| 0238011A2 | 9/1987 | European Pat. Off.. |
| 62-102388 | 6/1987 | Japan. |
| 62-155284 | 7/1987 | Japan. |
| 62-155285 | 7/1987 | Japan. |
| 63-295588A | 12/1988 | Japan. |
| 63-295589 | 12/1988 | Japan. |
| WO93/08809 | 5/1993 | WIPO. |
| PCT/US93/06974 | 10/1993 | WIPO. |

OTHER PUBLICATIONS

Abe et al., Annals of the New York Academy of Sciences 559:259–268, 1989, "Arachidonic Acid Metabolism in Ischemic Neuronal Damage".

Borasio, Neuroscience Letters 108:207–212, 1990, "Differential Effects of the Protein Kinase Inhibitor K–252A on the in Vitro Survival of Chick Embyronic".

Davis et al., J. Med. Chem. 35:177–184, 1992, "Inhibitors of Protein Kinase C. 1.1 2,3 Bisarylmaleimides".

Davis et al., FEBS Letters 259:61–63, 1989, "Potent Selective Inhibitors of Protein Kinase C".

Hara et al., Journal of Cerebral Blood Flow and Metabolism 10:646–653, 1990, "Staurosporine, A Novel Protein Kinase C Inhibitor, Prevents Postischemic Neuronal Damage in the Gerbil and Rat".

Hashimoto, The Journal of Cell Biology 107:1531–1539, 1988, "K–252A, A Potent Protein Kinase Inhibitor, Blocks Nerve Growth Factor–Induced Neurite Outgrowth . . . in Phosphorylation of Proteins in PC12H Cells".

Kase et al., The Journal of Antibiotics 39:1059–6219, 1986, "K–252A, A Potent Inhibitor of Protein Kinase C from Microbial Origin".

Kiyoto et al., Biochem. and Biophys. Research Communications 148:740–746, 1987, "Staurosporine, A Potent Protein Kinase C Inhibitor, Fails to Inhibit 12–O–Tetradecanoylphorbol–13–Acetate Caused . . . Cells".

Knüsel et al., Journal of Neurochemistry 57:955–961, 1991, "K–252B is a Selective and Monotoxic Inhibitor of Nerve Growth Factor Action on Cultured Brain Neurons".

Knüsel et al., Journal of Neurochemistry 59:715–722, 1992, "K–252B Selectively Potentiates Cellular Actions and TRK Tyrosine Phosphorylation Mediated by Neurotropin–3".

Koizumi et al., The Journal of Neuroscience 8:715–721, 1988, "K–252A: A Specific Inhibitors of the Action of Nerve Growth Factor on PC12 Cells".

Lazarovici et al., Journal of Neuroscience Research 23:1–8, 1989, "K–252A Inhibits the Increase in C–FOS Transcription and the Increase in Intracellular Calcium Produced by Nerve Growth Factor in PC12 Cells".

Matsuda et al., Biochem J. 256:75–80, 1988, "The Effect of K–252A, A Potent Microbial Inhibitor of Protein Kinase, on Activated Cyclic Nucleotide Phosphodiesterase".

Moody et al., J. Org. Chem. 57:2105–2114, 1992, "Synthesis of the Staurosporine Aglycon".

Nabeshima et al., The Journal of Pharmacology and Experimental Therapeutics 257:562–566, 1991, "Staurosporine Facilitates Recovery from the Basal Forebrain–Lesion–Induced Impairment of . . . Neuron in Rats".

Nakadate et al., Biochemical Pharmacology 37:1541–1545, 1988, "Comparison of Protein Kinase C Functional Assays to Clarify Mechanisms of Inhibitor Action".

Nakanishi et al., The Journal of Antibiotics 39:1066–1071, 1986, "K–252B, C and D, Potent Inhibitors of Protein Kinase C from Microbial Origin".

Sako et al., Cancer Research 48:4646–4650, 1988, "Contrasting Actions of Staurosporine, A protein Kinase C Inhibitor, on Human Neutrophils and Primary Mouse Epidermal Cells".

Shepherd, "The Synaptic Organization of the Brain" Second Edition, pp. 308–314 (Oxford University Press, New York, 1979).

Siman et al., Neuron 1:279–287, 1988, "Excitatory Amino Acids Activate Calpain I and Induce Structural Protein Breakdown in vivo".

Smith et al., Biochem. and Biophys. Research Communications 152:1497–1503, 1988, "Effects of a Protein Kinase C Inhibitor, K–252A, On Human Polymorphonuclear Neutrophil Responsiveness".

Steglich et al., Angew. Chem. Int. Ed. Engl. 19:459–460, 1980, "Indole Pigments from the Fruiting Bodies of the Slime Mold Arcyria Denudata".

Tischler et al., The Journal of Biological Chemistry 266:1141–1146, 1991, "A Protein Kinase Inhibitor, Staurosporine, Mimics Nerve Growth Factor Induction of Neurotensin/Neuromedin N Gene Expression".

Vitullo, Press Release "Cephalon and Kyowa Hakko Co., Ltd. Announce Collaboration," Jun. 2, 1992.

Wolf et al., Biochem. and Biophys. Research Communications 154:1273–1279, 1988, "The Protein Kinase Inhibitor Staurosporine, Like Phorbol Esters, Induces the Association of Protein Kinase C with Membranes".

Hirata, Chemical Abstracts, vol. 107, Issued 1987, Jul. 10, 1987 Abstract No. 236750y.

Hirata et al., Chemical Abstracts, vol. 107, Issued 1987, Abstract No. 2367512, Jul. 10, 1987.

Hirata et al., Chemical Abstracts, vol. 111, Issued 1989, Abstract No. 194456g (Dec. 1, 1988).

Akiyama et al., Chemical Abstracts, vol. 107, Issued 1987, Abstract No. 197943 (Jun. 1, 1987).

*Primary Examiner*—Philip I. Datlow
*Attorney, Agent, or Firm*—Fish & Richardson

[57] ABSTRACT

The invention features novel derivatives of K-252a, as well as novel bis-N-substituted derivatives of staurosporine. Also, a method for treating diseased neuronal cells involving the administration of either the novel staurosporine derivatives or specified functional derivatives of K-252a.

4 Claims, 14 Drawing Sheets

| COMPOUND | SPINAL CORD ChAT ACTIVITY | |
|---|---|---|
| | 300nM | 30nM |
| K-252a | 100 | - |
| II-44 | 146 | 80 |
| II-34 | 133 | 66 |
| II-47 | 126 | - |
| II-1 | 122 | - |
| II-31 | 120 | - |
| II-29 | 118 | 65 |
| II-32 | 118 | 70 |
| II-38 | 118 | - |
| II-2 | 111 | NT |
| II-3 | 109 | NT |
| II-46 | 109 | 84 |
| II-5 | 104 | NT |
| II-41 | 103 | - |
| II-42 | 102 | 64 |
| II-4 | 100 | - |
| II-30 | 94 | 71 |
| II-6 | 94 | - |
| II-7 | 90 | NT |
| II-39 | 90 | - |
| II-36 | 86 | - |
| II-8 | 85 | - |
| II-9 | 83 | 64 |
| II-10 | 81 | 143 |
| IV-3 | 77 | - |
| II-11 | 76 | NT |
| II-21 | 76 | 63 |
| III-1 | 75 | - |
| II-12 | 75 | - |
| IV-1 | 74 | 72 |
| II-13 | 73 | - |
| II-14 | 71 | - |

| COMPOUND | SPINAL CORD ChAT ACTIVITY | |
|---|---|---|
| | 300nM | 30nM |
| II-15 | 69 | - |
| II-18 | 68 | - |
| II-16 | 68 | - |
| II-17 | 68 | NT |
| II-40 | 66 | - |
| II-19 | 66 | - |
| II-20 | 65 | 65 |
| II-45 | 65 | - |
| II-22 | 62 | - |
| IV-2 | 62 | NT |
| III-2 | 60 | NT |
| II-25 | 58 | - |
| II-37 | 56 | - |
| II-23 | 55 | - |
| II-24 | 50 | - |
| II-26 | 39 | - |
| II-33 | - | 77 |
| II-43 | - | 125 |
| II-49 | - | 62 |
| II-50 | 84 | 56 |
| II-51 | 130 | 53 |
| II-52 | 103 | - |
| II-53 | 98 | 67 |
| II-54 | 51 | - |
| II-55 | 64 | - |
| II-56 | 88 | 53 |
| II-48 | 70 | - |

FIG. 13

NT = NOT TESTED AT THAT CONCENTRATION
- = NOT ACTIVE AT THAT CONCENTRATION

| COMPOUND AT 300nM | DRG SURVIVAL | |
|---|---|---|
| | %K-252a | %NGF |
| III-1 | NT | 69 |
| III-2 | NT | 61 |
| II-21 | 95* | NT |
| II-10 | 143 | 88 |
| II-19 | NT | 107 |
| II-15 | 105 | 158 |
| II-12 | 83 | 125 |
| II-17 | 77 | 116 |
| II-5 | 100 | 110 |
| II-13 | 73 | 110 |
| II-9 | 92 | 105 |
| II-4 | 83 | 95 |
| II-20 | 55 | 84 |
| II-1 | NT | 81 |
| II-2 | NT | 77 |
| II-23 | 83 | 73 |
| II-8 | NT | 68 |
| II-3 | NT | 84 |
| II-24 | 74 | 67 |
| II-25 | 68 | 62 |
| II-11 | 90 | 57 |
| II-6 | NT | 56 |
| II-32 | 106 | NT |
| II-30 | 75 | NT |

NT = NOT TESTED
* = ONLY ACTIVE AT 30nM

FIG. 14

EFFECT OF K-252a ON SURVIVAL OF STRIATAL NEURONS *IN VITRO*

75 nM K-252a

CONTROL

| COMPOUND | STRIATAL SURVIVAL | | %K-252a |
|---|---|---|---|
| | 25nM | 75nM | 100nM |
| K-252a | - | 100 | - |
| III-1 | 69 | NT | - |
| II-1 | 61 | NT | 104 |
| II-35 | 52 | 81 | - |
| II-20 | 58 | - | NT |
| II-10 | 91 | - | NT |
| II-28 | - | 90 | - |
| II-5 | 104 | NT | - |
| II-29 | 64 | NT | - |
| II-2 | 65 | - | NT |
| II-3 | 50 | 104 | - |
| II-30 | - | 114 | NT |
| II-6 | 81 | NT | - |
| II-31 | 92 | - | NT |
| II-32 | 69 | NT | - |
| IV-3 | - | NT | 47 |
| IV-1 | - | NT | 66 |
| II-33 | - | 82 | NT |
| II-34 | 118 | NT | - |

NT = NOT TESTED AT THAT CONCENTRATION

- = NOT ACTIVE AT THAT CONCENTRATION

FIG. 18

SELECTED PROTEIN KINASE INHIBITORS FOR THE TREATMENT OF NEUROLOGICAL DISORDERS

This application is a continuation-in-part of U.S. Ser. No. 07/920,102 filed on Jul. 24, 1992, now abandoned.

BACKGROUND OF THE INVENTION

Protein kinases are a broad class of enzymes which act to modify chemically many cellular proteins, by phosphorylation of amino acids.

Inhibitors of protein kinases are structurally varied, and have variable (and sometimes contradictory) effects on the nervous system and other tissues. A given protein kinase inhibitor may influence more than one protein kinase. For example, K-252a, an alkaloid-like material isolated from the culture broth of *Nocardiopsis sp.* and *Actinomadula sp.* was originally reported to be a protein kinase C inhibitor, but was subsequently found also to inhibit protein kinases A and G, myosin light-chain kinase, and trk (a tyrosine kinase activated by nerve growth factor [NGF], the latter a neurotrophic protein which promotes the survival of peripheral, sensory and sympathetic neurons).

Consistent with this latter effect, K-252a blocks the neurotrophic actions of NGF on PC-12 cells (chromaffin cells from rat adrenal medullary tumors, pheochromocytomas), and promotes the survival of dorsal root ganglion neurons and hippocampal neurons. However, it has been found to be cytotoxic at a wide range of concentrations, leading some investigators to conclude that it has limited usefulness in vivo.

A microbial alkaloid related to K-252a, staurosporine, also has a variety of effects on different protein kinases and cell types. Staurosporine was found to have NGF-like effects on PC-12 cells, and to protect the gerbil hippocampus from post-ischemic injury. It is able to reverse damage to cholinergic neurons in the rat basal forebrain.

K-252a and staurosporine have been proposed as tumor inhibitors. Staurosporine has been offered as an insecticide. Derivatives of staurosporine, with a hydrocarbyl radical or an acyl radical substituted at the methylamine nitrogen, have been made and proposed for the following uses: tumor inhibition, inflammation inhibition, immunomodulation, and treatment of diseases of the cardiovascular and central nervous systems.

SUMMARY OF THE INVENTION

The invention features, in one aspect, novel bis-N-substituted derivatives of staurosporine, represented by the formula

[Stau]-N(CH$_3$)—W—N(CH$_3$)-[Stau]     (I)

where [Stau] represents a residue of the formula

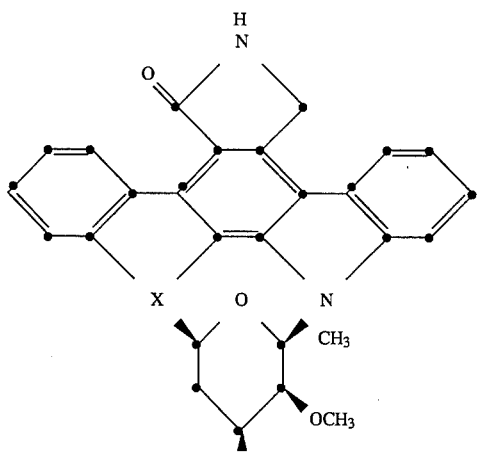

and W represents a bis(carbamyl) or bis(thiocarbamyl) radical,

—C(=Y)—NH—W'—NH—C(=Y)— where W' is a hydrocarbylene radical of 2–20 carbon atoms and Y is O or S.

The invention also features a novel derivative of K-252a, represented by the formula (II-4):

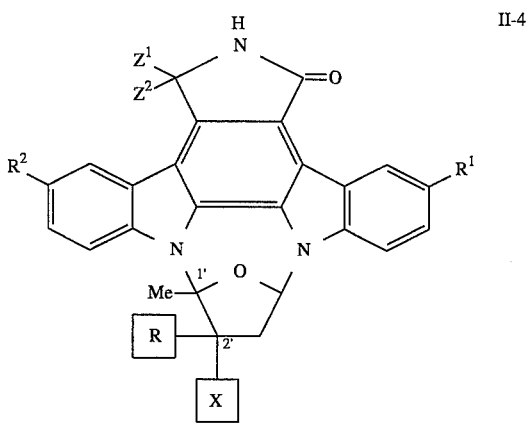

where R$^1$, R$^2$, Z$^1$ and Z$^2$ are each independently H, X is hydroxymethyl (CH$_2$OH), and R is OCH$_3$.

The invention also features a novel derivative of K-252a, represented by the formula:

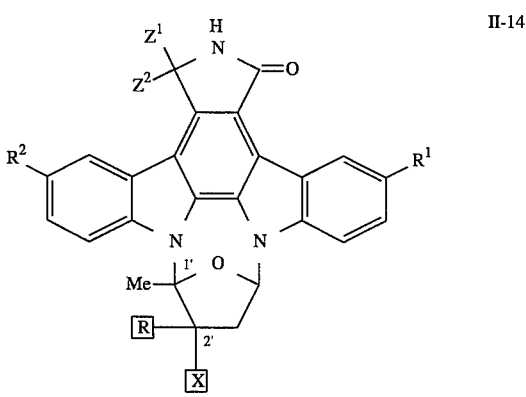

where R$^1$, R$^2$, Z$^1$ and Z$^2$ are each independently H, X is

CH₂—NH—Ser, and R is OH.

Also included in the invention are compounds represented by the following Formula (II-49):

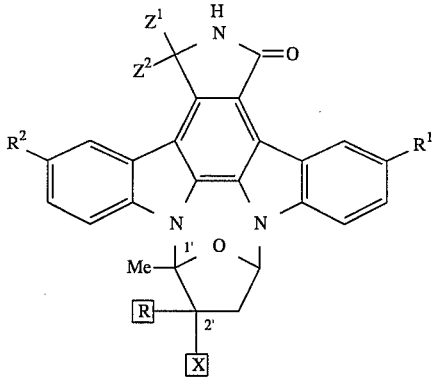

wherein $R^2$, $Z^1$, and $Z^2$ are each H, R is OH, $R^1$ is $CH_2SO_2C_2H_5$, and X is $CO_2CH_3$.

Also included in the invention are compounds represented by the following Formula (II-38):

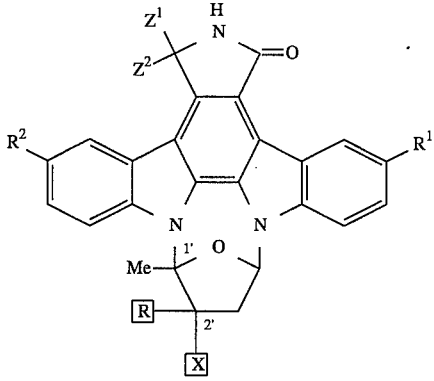

wherein $R^1$, $R^2$, $Z^1$, and $Z^2$ are each H, R is OH, and X is $CH_2NHCO_2C_6H_5$.

Also included in the invention are compounds represented by the following Formula (II-45):

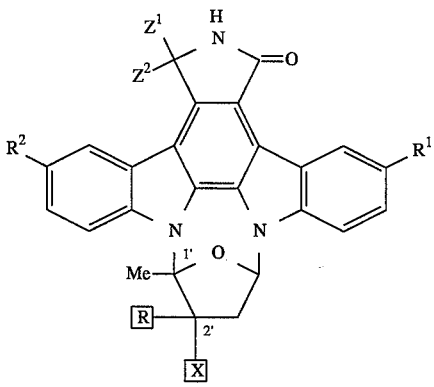

wherein $R^1$ and $R^2$ are each Br, R is OH, $Z^1$ and $Z^2$ are each H, and X is $CONHC_6H_5$.

Also included in the invention are compounds represented by the following Formula (II-57):

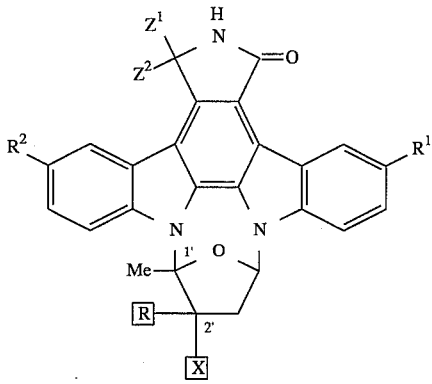

wherein $R^1$, $R^2$, $Z^1$, and $Z^2$ are each H, R is OH, and X is $CH_2NHCO_2CH_3$.

Also included in the invention are compounds represented by the following Formula (V):

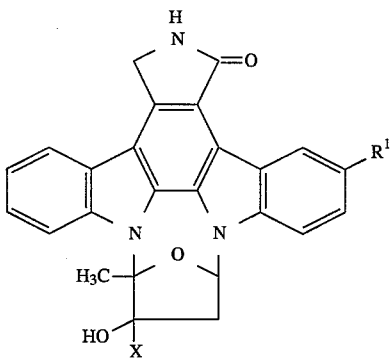

in which X represents $CO_2R^5$ (in which $R^5$ represents lower alkyl) or $CH_2NHCO_2R^6$ (in which $R^6$ represents lower alkyl or aryl); $R^1$ represents hydrogen or $CH_2SO_2R^7$ (in which $R^7$ represents lower alkyl), provided that the combination of $X=CO_2R^5$ and $R^1$=hydrogen is excluded.

In the definitions of the groups in Formula (V), lower alkyl means a straight-chain or branched alkyl group having 1 to 6 carbon atoms, preferably 1 to 3 carbon atoms, such as methyl, ethyl, propyl, isopropyl, butyl, isobutyl, sec-butyl, tert-butyl, pentyl, neopentyl, and hexyl. Aryl means an aryl group having 6 to 10 carbon atoms, such as phenyl and naphthyl.

Formula V compounds can be in the form of pharmaceutically acceptable salts. The pharmaceutically acceptable salts of Compounds (V) include pharmaceutically acceptable acid addition salts, metal salts, ammonium salts, organic amine addition salts, and amino acid addition salts.

Examples of the pharmaceutically acceptable acid addition salts are inorganic acid addition salts such as hydrochloride, sulfate, and phosphate, and organic acid addition salts such as acetate, maleate, fumarate, tartrate, and citrate. Examples of the pharmaceutically acceptable metal salts are alkali metal salts such as sodium salt and potassium salt, alkaline earth metal salts such as magnesium salt and calcium salt, aluminium salt, and zinc salt. Examples of the pharmaceutically acceptable ammonium salts are ammonium salt and tetraethyl ammonium salt. Examples of the pharmaceutically acceptable organic amine addition salts are salts with morpholine and piperidine. Examples of the pharmaceutically acceptable amino acid addition salts are salts with lysine, glycine, and phenylalanine.

In another aspect, the invention features a method for enhancing the function of cholinergic neurons, striatal neurons, and sensory neurons, e.g., dorsal root ganglion neurons, by administering to a mammal, e.g., a human, a therapeutic amount of one of the novel bis-substituted derivatives of staurosporine. The therapy may be given in conjunction with a neurotrophic factor, preferably a member of the neurotrophic family, and most preferably nerve growth factor (NGF). The neurotrophic family is a group of proteins with significant homology to NGF and include, in addition to NGF, brain-derived neurotrophic factor (BDNF; Leibrock et al., Nature 341:149–152, 1989); neutrophil-3 (NT-3; Hohn et al., Nature 344:339–341, 1990); and neurotrophic-5 (NT-5; Berkemeier et al., Neuron 7:857–866, 1991).

In another aspect, the invention features a method for protecting nerve cells of a mammal, e.g., a human, from degeneration induced by excitatory amino acids, by administering to the mammal a therapeutic amount of one of the novel bis-substituted derivatives of staurosporine. Conditions in which such degeneration may occur include Alzheimer's disease; motor neuron disease, e.g., amyotrophic lateral sclerosis; Parkinson's disease; cerebrovascular disease, e.g., ischemic conditions; AIDS dementia; epilepsy; Huntington's disease; and concussive or penetrating injuries to the brain or spinal cord. The therapy may be given in conjunction with a neurotrophic factor, preferably a member of the neurotrophin family, most preferably nerve growth factor (NGF).

In another aspect, the invention features a method for enhancing the function of cholinergic neurons, striatal neurons, and sensory neurons, e.g., dorsal root ganglion neurons, in a mammal, e.g., a human, by administering to the mammal a therapeutic amount of a functional derivative of K-252a, represented by the formulas

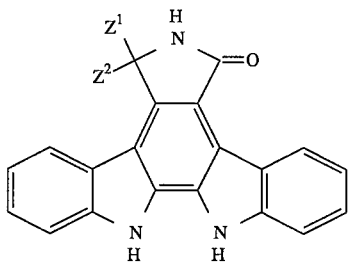

III or

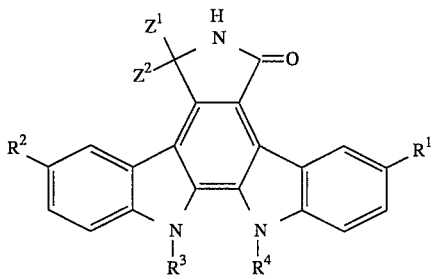

IV with any of the following substitutions:

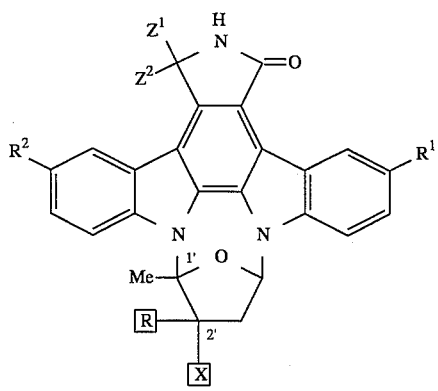

II

TABLE 1

| Compound | $R^1$ | $R^2$ | X | R | $Z^{1(1)}$ $Z^2$ |
|---|---|---|---|---|---|
| II-1 | H | H | $CH_2N_3$ | OH | H |
| II-2 | $NHCONHC_6H_5$ | H | $CO_2CH_3$ | OH | H |
| II-3 | $CH_2SOC_2H_5$ | H | $CO_2CH_3$ | OH | H |
| II-4 | H | H | $CH_2OH$ | $OCH_3$ | H |
| II-5 | H | H | $CONHC_2H_5$ | OH | H |

TABLE 1-continued

| Compound | $R^1$ | $R^2$ | X | R | $Z^{1(1)}$ $Z^2$ |
|---|---|---|---|---|---|
| II-6 | H | H | CH=NNH—(2-imidazolinyl) | OH | H |
| II-7[2,7] | H | H | $CH_2NH$—Gly | OH | H |
| II-8 | H | H | $CON(CH_3)_2$ | OH | H |
| II-9[3] | H | H | —$CH_2NHCO_2$— | | H |
| II-10 | Br | H | $CO_2CH_3$ | OH | H |
| II-11 | H | H | $CONH_2$ | OH | H |
| II-12 | H | H | $CH_2OH$ | OH | H |
| III-1 | — | H | — | — | H |
| II-13 | H | H | $CONHC_3H_7$ | OH | H |
| II-14[2] | H | H | $CH_2NH$—Ser | OH | H |
| II-15 | H | H | $CH_2SOCH_3$ | OH | H |
| II-16 | H | H | CH=NOH | OH | H |
| II-17 | H | H | CON(morpholino) | OH | H |
| II-18[2,7] | H | H | $CH_2NH$—Pro | OH | H |
| II-19 | H | H | $CH=NNHC(=NH)NH_2$ | OH | H |
| II-20 | Br | Br | $CO_2CH_3$ | OH | O |
| II-21 | H | H | $CONH(CH_2)_2OH$ | OH | H |
| II-22 | H | H | $CO_2CH_3$ | OH | O |
| III-2 | — | H | — | — | O |
| II-23 | H | H | H | OH | H |
| II-24 | H | H | $CH=NNHCONH_2$ | OH | H |
| II-25 | H | H | $CH_2OCOCH_3$ | OH | H |
| II-26[3] | H | H | —$CH_2OC(CH_3)_2O$— | | H |
| II-29 | $NHCONHC_2H_5$ | H | $CO_2CH_3$ | OH | H |
| II-30 | $CH_2SC_2H_5$ | H | $CO_2CH_3$ | OH | H |
| II-31 | Br | H | $CH_2OH$ | •OH | H |
| II-32 | Br | Br | $CO_2CH_3$ | OH | H |
| II-33 | $CH_2SC_6H_5$ | H | $CO_2CH_3$ | OH | H |
| II-34 | Cl | Cl | $CO_2CH_3$ | OH | H |
| II-36 | H | H | $CONHC_6H_5$ | OH | H |
| II-37 | H | H | $CH_2SO$-(2-pyridyl) | OH | H |
| II-38 | H | H | $CH_2NHCO_2C_6H_5$ | OH | H |
| II-39 | $NHCONHC_2H_5$ | $NHCONHC_2H_5$ | $CO_2CH_3$ | OH | H |
| II-40 | $N(CH_3)_2$ | H | $CO_2CH_3$ | OH | H |
| II-41 | $CH_3$ | H | $CO_2CH_3$ | OH | H |
| II-42 | $CH_2OCONHC_2H_5$ | H | $CO_2CH_3$ | OH | H |
| II-43 | $NHCO_2CH_3$ | H | $CO_2CH_3$ | OH | H |
| II-44 | Br | Br | $CH_2OH$ | OH | H |
| II-45 | Br | Br | $CONHC_6H_5$ | OH | H |
| II-46 | Br | Br | $CONHCH_2CH_2OH$ | OH | H |
| II-47 | $CH_2OC_2H_5$ | H | $CO_2CH_3$ | OH | H |
| II-48 | $CH_2N(CH_3)_2$ | H | $CO_2CH_3$ | OH | H |
| II-49 | $CH_2SO_2C_2H_5$ | H | $CO_2CH_3$ | OH | H |
| II-50 | $CH_2S$-(2-pyridyl) | H | $CO_2CH_3$ | OH | H |
| II-51 | $CH_2SC_2H_5$ | $CH_2SC_2H_5$ | $CO_2CH_3$ | OH | H |
| II-52 | CH=NNH-(2-imidazolinyl) | H | $CO_2CH_3$ | OH | H |

TABLE 1-continued

| Compound | R¹ | R² | X | R | $Z^{1(1)}$ $Z^2$ |
|---|---|---|---|---|---|
| II-53 | CH₂S-[pyrimidinyl] | H | CO₂CH₃ | OH | H |
| II-54 | CH₂S(O)-[pyrimidinyl] | H | CO₂CH₃ | OH | H |
| II-55 | CH₂S(O)-[pyridyl] | H | CO₂CH₃ | OH | H |
| II-56 | CH₂SC₂H₅ | CH₂OH | CO₂CH₃ | OH | H |
| II-57 | H | H | CH₂NHCO₂CH₃ | OH | H |
| II-58 | Br | H | CONH₂ | OH | H |
| II-59 | H | H | CH₂SC₆H₅ | OH | H |
| II-60 | H | H | CH₂S-[pyridyl] | OH | H |
| II-61 | H | H | CH₂SOC₆H₅ | OH | H |
| IV-1[(4,9)] | H | H | — | — | H |
| IV-2[(5)] | Br | H | — | — | H |
| IV-3[(6)] | H | H | — | — | H |
| IV-4[(8,9)] | H | H | — | — | H |

[(1)]$Z^1$ and $Z^2$ are both hydrogen, or both are combined together to represent oxygen, where indicated.
[(2)]NH-amino acid linkage is an amide bond through the carboxyl group of the amino acid.
[(3)]X and R are combined together to form the linking group.
[(4)]$R^3$ is CH₂CH=CH₂; $R^4$ is H.
[(5)]$R^3$ and $R^4$ are each H.
[(6)]$R^3$ and $R^4$ are each CH₂CH=CH₂.
[(7)]Compound is in the form of the hydrochloride.
[(8)]$R^3$ is H and $R^4$ is CH₂CH=CH₂.
[(9)]IV-1 and IV-4 is a 1.5 to 1.0 mixture of the two components.

The therapy may be given in conjunction with a neurotrophic factor, preferably a member of the neurotrophin family, most preferably nerve growth factor (NGF). The method may be used to treat Huntington's disease.

In a preferred aspect, the invention features a method for enhancing the function of a dorsal root ganglion nerve cell, by administering to a mammal, e.g., a human, a therapeutic amount of a functional derivative of K-252a, represented by the formula (II) or (III)

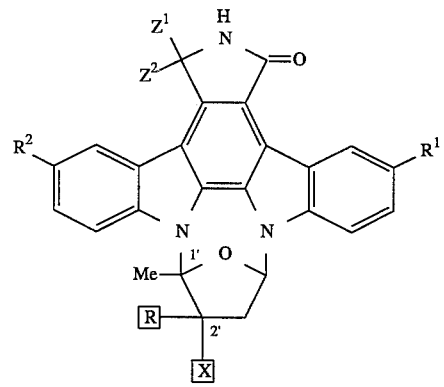

(II)

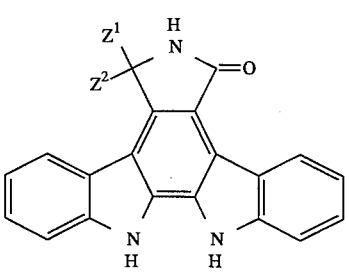

(III)

wherein the following substitutions are made:

TABLE 2

| Compound[1] | R[1] | X | R | $Z^{1[2]}$ $Z^2$ |
|---|---|---|---|---|
| II-1 | H | $CH_2N_3$ | OH | H |
| II-2 | $NHCONHC_6H_5$ | $CO_2CH_3$ | OH | H |
| II-3 | $CH_2SOC_2H_5$ | $CO_2CH_3$ | OH | H |
| II-4 | H | $CH_2OH$ | $OCH_3$ | H |
| II-5 | H | $CONHC_2H_5$ | OH | H |
| II-6 | H | CH=NNH—(imidazoline) | OH | H |
| II-8 | H | $CON(CH_3)_2$ | OH | H |
| II-9[3] | H | —$CH_2NHCO_2$— | | H |
| II-10 | Br | $CO_2CH_3$ | OH | H |
| II-11 | H | $CONH_2$ | OH | H |
| II-12 | H | $CH_2OH$ | OH | H |
| III-1 | — | — | — | H |
| II-13 | H | $CONHC_3H_7$ | OH | H |
| II-15 | H | $CH_2SOCH_3$ | OH | H |
| II-17 | H | CON(morpholine) | OH | H |
| II-19 | H | $CH=NNHC(=NH)NH_2$ | OH | H |
| II-20[1] | Br | $CO_2CH_3$ | OH | O |
| II-21 | H | $CONH(CH_2)_2OH$ | OH | H |
| III-2 | — | — | — | O |
| II-23 | H | H | OH | H |
| II-24 | H | $CH=NNHCONH_2$ | OH | H |
| II-25 | H | $CH_2OCOCH_3$ | OH | H |
| II-30 | H | $CH_2SC_2H_5$ | $CO_2CH_3$ | OH | H |
| II-32 | Br | $CO_2CH_3$ | OH | H |

[1]$R^2$ is hydrogen, except in compound II-20 and II-32 where $R^2 =$ Br.
[2]$Z^1$ and $Z^2$ are both hydrogen, or both are combined together to represent oxygen, where indicated.
[3]X and R are combined together to form the linking group.

The therapy may be given in conjunction with a neurotrophic factor, preferably a member of the neurotrophin family, most preferably nerve growth factor (NGF).

In a preferred aspect, the invention features a method for enhancing the function of cholinergic neurons of a mammal, e.g., a human, by administering to the mammal a therapeutic amount of K-252a, represented by the formula (II):

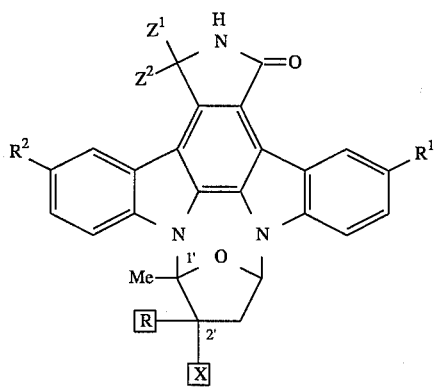

wherein $R^1$ and $R^2$ are each H, X is $CO_2CH_3$, R is OH, and $Z^1$ and $Z^2$ are each H. The therapy may be given in conjunction with a neurotrophic factor, preferably a member of the neurotrophin family, most preferably nerve growth factor (NGF), and may be used to treat Huntington's disease.

In a preferred aspect, the invention features a method for enhancing the survival and/or function of a striatal nerve cell, by administering to a mammal, e.g., a human, a therapeutic amount of K-252a or a functional derivative of K-252a, represented by the formula (II), (III), or (IV):

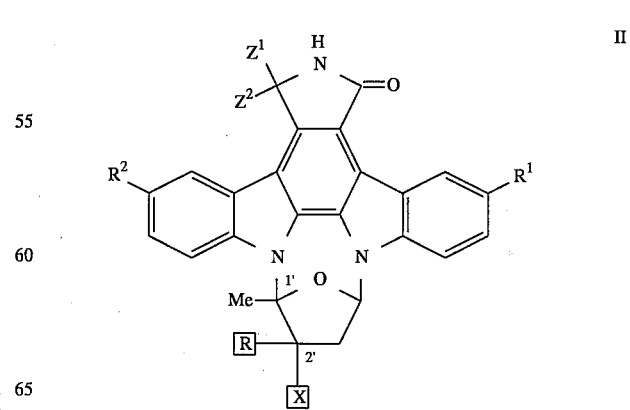

-continued

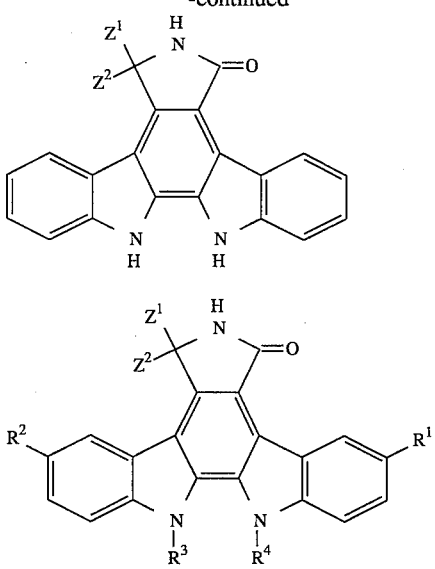

III

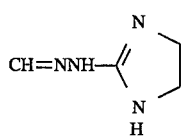

IV wherein the following substitutions are made:

TABLE 3

| Compound | R¹ | R² | X | R | Z²⁽¹⁾ Z¹ |
|---|---|---|---|---|---|
| K-252a | H | H | $CO_2CH_3$ | OH | H |
| III-1 | — | H | — | — | H |
| II-1 | H | H | $CH_2N_3$ | OH | H |
| II-35 | H | H | $CO_2$n-$C_6H_{13}$ | OH | H |
| II-20 | Br | Br | $CO_2CH_3$ | OH | O |
| II-10 | Br | H | $CO_2CH_3$ | OH | H |
| II-28 | O-n-$C_3H_7$ | H | $CO_2CH_3$ | OH | H |
| II-5 | H | H | $CONHC_2H_5$ | OH | H |
| II-29 | $NHCONHC_2H_5$ | H | $CO_2CH_3$ | OH | H |
| II-2 | $NHCONHC_6H_5$ | H | $CO_2CH_3$ | OH | H |
| II-3 | $CH_2SOC_2H_5$ | H | $CO_2CH_3$ | OH | H |
| II-30 | $CH_2SC_2H_5$ | H | $CO_2CH_3$ | OH | H |
| II-6 | H | H | CH=NNH-(imidazole) | OH | H |
| II-31 | Br | H | $CH_2OH$ | OH | H |
| II-32 | Br | Br | $CO_2CH_3$ | OH | H |
| IV-1⁽²⁾ | — | H | — | — | H |
| II-33 | $CH_2SC_6H_5$ | H | $CO_2CH_3$ | OH | H |
| II-34 | Cl | Cl | $CO_2CH_3$ | OH | H |

⁽¹⁾$Z^1$ and $Z^2$ are both hydrogen, or both are combined together to represent oxygen, where indicated.
⁽²⁾$R^3$ is $CH_2$—CH=$CH_2$; $R^4$ is H.

The therapy may be given in conjunction with a neurotrophic factor, preferably a member of the neurotrophin family, most preferably nerve growth factor, and may be used to treat Huntington's disease.

Other features and advantages of the invention will be apparent from the following description of the preferred embodiments thereof, and from the claims.

DESCRIPTION OF THE PREFERRED EMBODIMENTS

The drawings are first described.

Drawings FIG. 1 is a graph illustrating the effect of K-252a, 1,6-hexamethylene-bis-(carbamylstaurosporine) (HBCS), and staurosporine on basal ornithine decarboxylase (ODC) activity in PC-12 cells.

FIG. 13 is a table showing the relative activity of K-252a derivatives on ChAT activity in rat spinal cord cultures.

FIG. 14 is a table showing the relative activity of K-252a derivatives on neuronal survival in chick dorsal root ganglion cultures.

FIG. 15 is a graph illustrating survival of striatal neurons in the presence of K-252a.

FIG. 16 is a graph illustrating survival of striatal cells in the presence of K-252a.

FIG. 17 is a photomicrograph of striatal neurons cultured in the presence or absence of K-252a.

FIG. 18 is a table showing the relative activity of K-252a derivatives on neuronal survival in rat striatal cultures.

Staurosporine Derivatives

Figure 1:
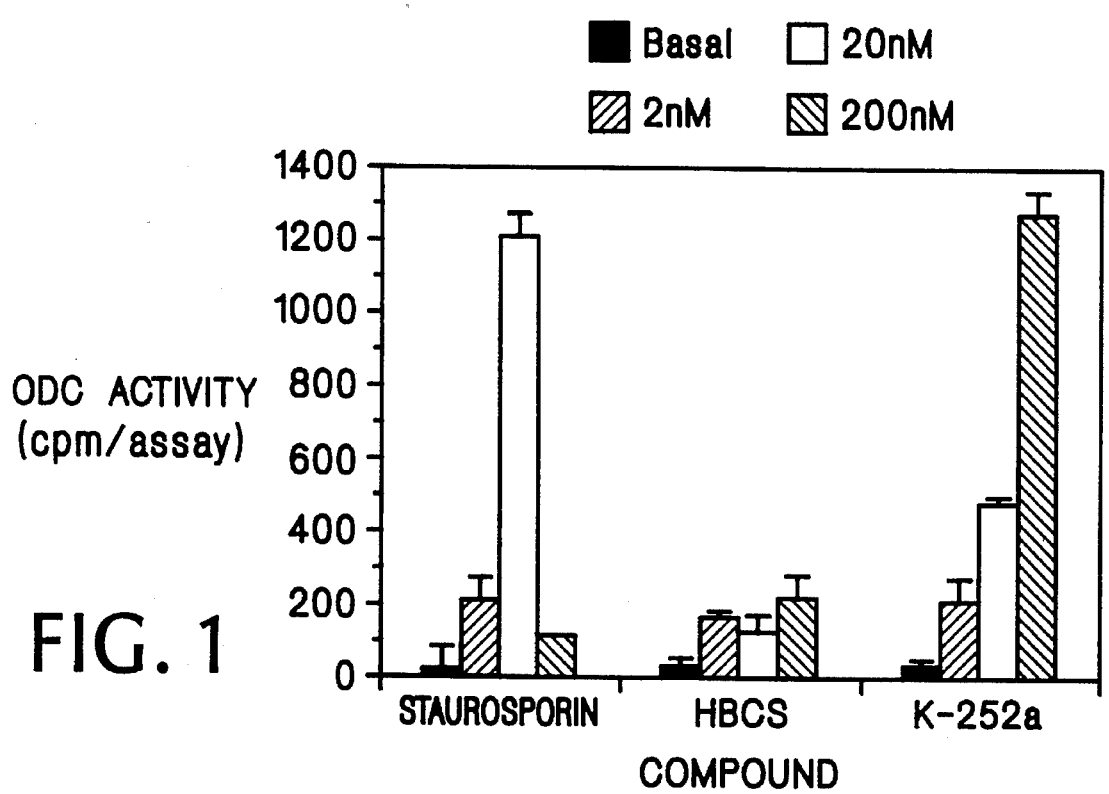

The present invention relates to novel bis-N-substituted derivatives of staurosporine and their use as therapeutics for neurological diseases, especially those diseases characterized either by neuronal cells which are injured, compromised, undergoing axonal degeneration, or at increased risk of dying, or by impaired cholinergic activity. These diseases include those induced by excitatory amino acids. The therapeutic use of these novel derivatives includes use of the derivatives alone and use of the derivatives combined with exogenous administration of neurotrophic factors (preferably members of the neurotrophin family, most preferably nerve growth factor, NGF). The compounds within the scope of this invention may be represented by the formula

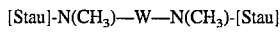

in which [Stau] represents a residue of the formula:

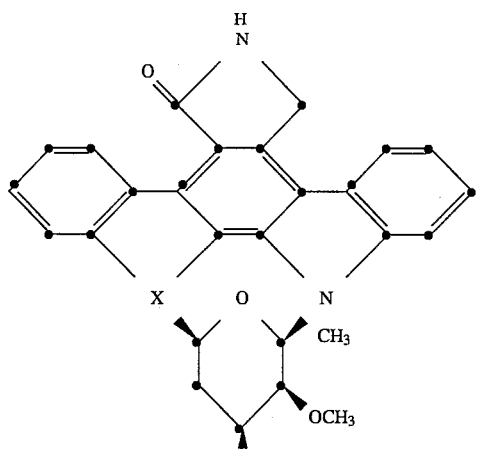

and W represents a bis(carbamyl) or bis(thiocarbamyl) radical, $$-C(=Y)-NH-W'-NH-C(=Y)-$$

in which W' is a hydrocarbylene radical of 2–20 carbon atoms and Y is O or S. W' is preferably an alkylene radical of 2–10 carbons, unsubstituted, or substituted with 1–3 alkyl groups of 1–3 carbons; an arylene radical of 6–12 carbons, unsubstituted, or substituted with 1–3 alkyl groups of 1–3 carbons, chlorine or bromine. W' is especially preferably hexamethylene and 1,4-phenylene. Y is preferably O.

Compounds of formula (I) can be prepared by procedures known in the art for preparation of carbamates and thiocarbamates. Preferably, the compounds are prepared by reaction of a bis-diisocyanate or a bis-diisothiocyanate with staurosporine to give a compound of formula (I) wherein Y=O or Y=S respectively.

Intermediate bis-diisocyanates and bis-diisothiocyanates suitable for use include:
1,6-diisocyanatohexane
toluene-2,6-diisocyanate
benzene-1,2-diisocyanate
2-methyl-1,5-diisocyanatopentane
naphthalene-2,6 diisocyanate
1,6-diisothiocyanatohexane
1,4-diisothiocyanatobutane
toluene-2,4-diisocyanate
benzene-1,4-diisocyanate
1,2-diisocyanatoethane
naphthalene-1,5-diisocyanate
1,5-diisocyanatopentane
benzene-1,4-diisothiocyanate
2-methyl-1,5-diisothiocyanatopentane
For reviews of the preparation of isocyanates and isothiocyanates, see the article by Richter and Ulrich, pp. 619–818, in Patai, "The Chemistry of Cyanates and Their Thio Derivatives", Part 2, Wiley, N.Y., 1977. The compounds are preferably prepared by reaction of phosgene (Y=O) or thiophosgene (Y=S) with the corresponding diamine. Alternative methods of preparation may also be employed. For example, 1,2-diisocyanatoethane may be prepared by reaction of ethylene urea with phosgene followed by heating.

K-252a Derivatives

The present invention is also directed to the use of specific functional derivatives of K-252a, as therapeutics in certain neurological diseases or disturbances characterized by neurons which are injured, compromised, undergoing axonal degeneration, or at risk of dying. The functional derivatives may be administered alone or in conjunction with a neurotrophic factor (preferably a member of the neurotrophin family, most preferably nerve growth factor, NGF). A "functional derivative" of K-252a is defined as a modified form of that molecule, which possesses the desired biological activity, herein defined as neuroprotective activity, for example the ability to promote nerve cell survival, or to promote nerve fiber (e.g. axonal) growth, or to enhance cholinergic nerve cell function, or to enhance the function of sensory cells, e.g., dorsal root ganglion nerve cells, or to enhance the function and/or survival of striatal neurons. Such molecular modifications may improve the molecule's solubility, absorption, transport (e.g., through the blood-brain barrier and cellular membranes), biological halflife, etc. Alternatively, or in addition, some moieties may decrease the toxicity of the molecule, or eliminate or attenuate any undesirable side effect of the molecule.

The compounds within the scope of the invention may be represented by formula (II) [hereinafter referred to as compound (II)], formula (III) [hereinafter referred to as compound (III)], and formula (IV) [hereinafter referred to as compound (IV)], below:

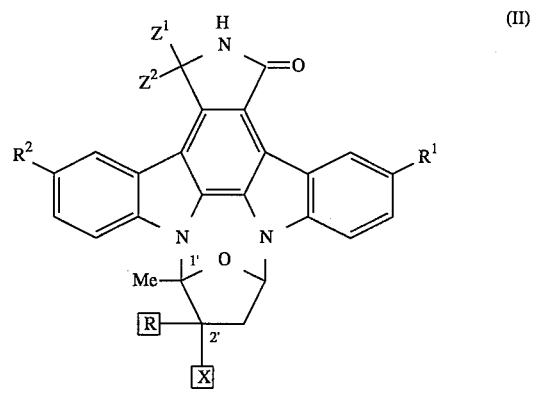

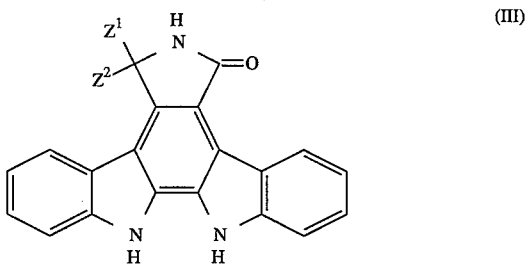

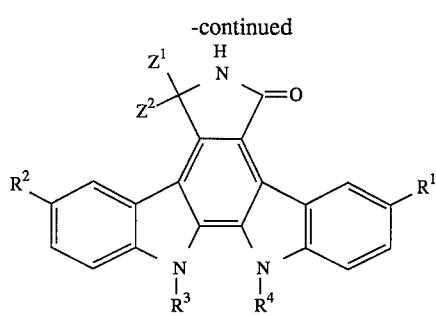

(IV)

with substitutions in Table 4, below, depicting the compounds within the scope of the invention. The functional derivatives of K-252a of the invention may be prepared de novo by chemical synthesis using methods known to those skilled in the art. For example, procedures used for preparation of Compound II are described by Murakata et al (U.S. Pat. No. 4,923,986), hereby incorporated by reference. Procedures used for preparation of Compound III are described by Moody et al., J. Org. Chem. 57: 2105–2114 (1992); Steglich et al., Angew. Chem. Int. Ed. Engl. 19: 459–460 (1980); Nakanishi et al., J. Antibiotics 39: 1066–1071 (1986); and Japanese Patent Application No. 60-295172 (1985). Further methods are described for compounds II-1, 9, 12 and 15 in Japanese Patent Application No. 60-295173 (1985); compounds II-2, 3, 4, 24, 25 and 26 in Japanese Patent Application No. 62-327858 (1987); compounds II-20 in Japanese Patent Application No. 62-327859 (1987); and compounds II-10 in Japanese Patent Application No. 60-257652 (1985) by Meiji Seika Kaisha Ltd.

TABLE 4 +HC,1 +UZ,15/33 Functional Derivatives of K-252a+HU (10)?

| Compound | $R^1$ | $R^2$ | X | R | $Z^{1(1)}$ $Z^2$ |
|---|---|---|---|---|---|
| II-1 | H | H | $CH_2N_3$ | OH | H |
| II-2 | $NHCONHC_6H_5$ | H | $CO_2CH_3$ | OH | H |
| II-3 | $CH_2SOC_2H_5$ | H | $CO_2CH_3$ | OH | H |
| II-4 | H | H | $CH_2OH$ | $OCH_3$ | H |
| II-5 | H | H | $CONHC_2H_5$ | OH | H |
| II-6 | H | H | CH=NNH—(imidazole) | | |
| II-7[(2,7)] | H | H | $CH_2NH$—Gly | OH | H |
| II-8 | H | H | $CON(CH_3)_2$ | OH | H |
| II-9[(3)] | H | H | —$CH_2NHCO_2$— | | H |
| II-10 | Br | H | $CO_2CH_3$ | OH | H |
| II-11 | H | H | $CONH_2$ | OH | H |
| II-12 | H | H | $CH_2OH$ | OH | H |
| III-1 | — | H | — | — | H |
| II-13 | H | H | $CONHC_3H_7$ | OH | H |
| II-14[(2)] | H | H | $CH_2NH$—Ser | OH | H |
| II-15 | H | H | $CH_2SOCH_3$ | OH | H |
| II-16 | H | H | CH=NOH | OH | H |
| II-17 | H | H | CON(morpholine) | OH | H |
| II-18[(2,7)] | H | H | $CH_2NH$—Pro | OH | H |
| II-19 | H | H | CH=NNHC(=NH)$NH_2$ | OH | H |
| II-20 | Br | Br | $CO_2CH_3$ | OH | O |
| II-21 | H | H | $CONH(CH_2)_2OH$ | OH | H |
| II-22 | H | H | $CO_2CH_3$ | OH | O |
| III-2 | — | H | — | — | O |
| II-23 | H | H | H | OH | H |
| II-24 | H | H | CH=$NNHCONH_2$ | OH | H |
| II-25 | H | H | $CH_2OCOCH_3$ | OH | H |
| II-26[(3)] | H | H | —$CH_2OC(CH_3)_2O$— | | H |
| II-29 | $NHCONHC_2H_5$ | H | $CO_2CH_3$ | OH | H |
| II-30 | $CH_2SC_2H_5$ | H | $CO_2CH_3$ | OH | H |
| II-31 | Br | H | $CH_2OH$ | OH | H |
| II-32 | Br | Br | $CO_2CH_3$ | OH | H |
| II-33 | $CH_2SC_6H_5$ | H | $CO_2CH_3$ | OH | H |
| II-34 | Cl | Cl | $CO_2CH_3$ | OH | H |
| II-36 | H | H | $CONHC_6H_5$ | OH | H |
| II-37 | H | H | $CH_2SO$-(N-piperidinyl phenyl) | OH | H |
| II-38 | H | H | $CH_2NHCO_2C_6H_5$ | OH | H |
| II-39 | $NHCONHC_2H_5$ | $NHCONHC_2H_5$ | $CO_2CH_3$ | OH | H |

TABLE 4 +HC,1 +UZ,15/33 Functional Derivatives of K-252a+HU (10)?-continued

| Compound | $R^1$ | $R^2$ | X | R | $Z^{1(1)}$ $Z^2$ |
|---|---|---|---|---|---|
| II-40 | $N(CH_3)_2$ | H | $CO_2CH_3$ | OH | H |
| II-41 | $CH_3$ | H | $CO_2CH_3$ | OH | H |
| II-42 | $CH_2OCONHC_2H_5$ | H | $CO_2CH_3$ | OH | H |
| II-43 | $NHCO_2CH_3$ | H | $CO_2CH_3$ | OH | H |
| II-44 | Br | Br | $CH_2OH$ | OH | H |
| II-45 | Br | Br | $CONHC_6H_5$ | OH | H |
| II-46 | Br | Br | $CONHCH_2CH_2OH$ | OH | H |
| II-47 | $CH_2OC_2H_5$ | H | $CO_2CH_3$ | OH | H |
| II-48 | $CH_2N(CH_3)_2$ | H | $CO_2CH_3$ | OH | H |
| II-49 | $CH_2SO_2C_2H_5$ | H | $CO_2CH_3$ | OH | H |
| II-50 | $CH_2S$-(pyridyl) | H | $CO_2CH_3$ | OH | H |
| II-51 | $CH_2SC_2H_5$ | $CH_2SC_2H_5$ | $CO_2CH_3$ | OH | H |
| II-52 | $CH=NNH$-(imidazolyl) | H | $CO_2CH_3$ | OH | H |
| II-53 | $CH_2S$-(pyridyl) | H | H | $CO_2CH_3$ | OH | H |
| II-54 | $CH_2S(O)$-(pyridyl) | H | $CO_2CH_3$ | OH | H |
| II-55 | $CH_2S(O)$-(pyridyl) | H | $CO_2CH_3$ | OH | H |
| II-56 | $CH_2SC_2H_5$ | $CH_2OH$ | $CO_2CH_3$ | OH | H |
| II-57 | H | H | $CH_2NHCO_2CH_3$ | OH | H |
| II-58 | Br | H | $CONH_2$ | OH | H |
| II-59 | H | H | $CH_2SC_6H_5$ | OH | H |
| II-60 | H | H | $CH_2S$-(pyridyl) | OH | H |
| II-61 | H | H | $CH_2SOC_6H_5$ | OH | H |
| IV-1[(4,9)] | H | H | — | — | H |
| IV-2[(5)] | Br | H | — | — | H |
| IV-3[(6)] | H | H | — | — | H |
| IV-4[(8,9)] | H | H | — | — | H |

[(1)]$Z^1$ and $Z^2$ are both hydrogen, or both are combined together to represent oxygen, where indicated.
[(2)]NH-amino acid linkage is an amide bond through the carboxyl group of the amino acid.
[(3)]X and R are combined together to form the linking group.
[(4)]$R^3$ is $CH_2CH=CH_2$; $R^4$ is H.
[(5)]$R^3$ and $R^4$ are each H.
[(6)]$R^3$ and $R^4$ are each $CH_2CH=CH_2$.?
[(7)]Compound is in the form of the hydrochloride.
[(8)]$R^3$ is H and $R^4$ is $CH_2CH=CH_2$.
[(9)]IV-1 and IV-4 is a 1.5 to 1.0 mixture of the two components.
[(10)]For K-252a itself, $R^1 = R^2 = H$, $X = CO_2CH_3$, $R = OH$, $Z^1$ and $Z^2 = H$.

The invention also involves a method for enhancing the function of cholinergic neurons, by administration of a therapeutic amount of K-252a, represented by the formula (II) given above and substitutions shown in Table 4, (note 10). This compound is prepared by procedures described in the art (see Matsuda et al., U.S. Pat. No. 4,554,402; Kase et al., J. Antibiotics 37: 1059–1065 [1986]). By "enhancing the function of cholinergic neurons" is meant promoting cholinergic nerve cell survival, and/or nerve fiber (e.g. axonal) growth, and/or enhancing cholinergic activity of nerve cells. K-252a may be administered with or without a neurotrophic factor, preferably a member of the neurotrophin family, most preferably nerve growth factor (NGF).

Uses of the Compounds

As described more fully below, the present invention provides novel uses of functional derivatives of K-252a or compounds of Formula I, either alone or in combination with neurotrophic factors such as NGF, as therapeutics for neurological diseases, especially those diseases characterized either by neuronal cells which are injured, compromised, undergoing axonal degeneration, or at increased risk of dying, or by impaired cholinergic activity. These diseases include those induced by excitatory amino acids. The bioactivity of the compounds of the invention, including the combination with a neurotrophic factor, may conveniently be assayed by a cultured PC-12 cell ornithine decarboxylase assay, a cultured spinal cord choline acetyltransferase assay, a cultured dorsal root ganglion neuron survival assay, a cultured striatal neuron survival assay, or an in vivo excitotoxin neuroprotection assay, all of which are described in detail below. Thus, the compounds of this invention are useful for administration to humans or other mammals who suffer from neurological diseases or disturbances characterized by increased risk of neuronal cell death or dysfunction, as described above. These neurological diseases and disturbances include but are not limited to: Alzheimer's disease; motor neuron disease including amyotrophic lateral sclerosis; Parkinson's disease; stroke or other ischemic injuries; Huntington's disease; AIDS dementia; epilepsy; concussive or penetrating injuries of the brain or spinal cord; and peripheral neuropathies.

The compounds provided herein can be formulated into pharmaceutical compositions by admixture with pharmaceutically acceptable nontoxic excipients and carriers. As noted above, such compositions may be prepared for use in parenteral administration, particularly in the form of liquid solutions or suspensions; for oral administration, particularly in the form of tablets or capsules; or intranasally, particularly in the form of powders, nasal drops, or aerosols.

The composition may conveniently be administered in unit dosage form and may be prepared by any of the methods well known in the pharmaceutical art, for example, as described in *Remington's Pharmaceutical Sciences* (Mack Pub. Co, Easton, Pa., 1980). Formulations for parenteral administration may contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or citric acid for vaginal administration.

The materials of this invention can be employed as the sole active agent in a pharmaceutical or can be used in combination with other active ingredients, e.g., other growth factors which could facilitate neuronal survival or axonal growth in neurological diseases or disorders, for example, peripheral neuropathy.

The concentrations of the compounds described herein in a therapeutic composition will vary depending upon a number of factors, including the dosage of the drug to be administered, the chemical characteristics (e.g., hydrophobicity) of the compounds employed, and the route of administration. In general terms, the compounds of this invention may be provided in an aqueous physiological buffer solution containing about 0.1 to 10% w/v compound for parenteral administration. Typical dose ranges are from about 1 μg/kg to about 1 g/kg of body weight per day; a preferred dose range is from about 0.01 mg/kg to 100 mg/kg of body weight per day. The preferred dosage of drug to be administered is likely to depend on such variables as the type and extent of progression of the neurological disease, the overall health status of the particular patient, the relative biological efficacy of the compound selected, the formulation of the compound excipients, and its route of administration.

The present invention will be further illustrated by the following examples. These examples are not to be construed as limiting the scope of the invention, which is to be determined solely by the appended claims.

EXAMPLE 1

1,6-Hexamethylene-bis-(carbamylstaurosporine) (HBCS)

A solution of 1.0 mg (2.15 micromoles) of staurosporine (Kamiya Biomedical Company, Thousand Oaks, Calif.) in 1.00 ml of ethyl acetate (dried over anhydrous magnesium sulfate) was treated with 17 microliters (1.08 micromoles) of a solution of 10.75 mg of hexamethylene-bis-isocyanate in 1.0 ml of dried ethyl acetate. The reaction mixture in an amber glass reaction vial was allowed to stand at room temperature for two days. A crystalline deposit weighing 600 micrograms was separated. Its composition was verified by fast atom bombardment mass spectroscopy (FAB-MS).

| $M + H^+$ Calculated = 1102 | $M + Na^+$ Calculated = 1124 |
|---|---|
| Found = 1102 | Found = 1124 |

This product and all of the subsequently described staurosporine derivatives were stored in non-actinic glass vials.

EXAMPLE 2 p-Phenylene-bis-(carbamylstaurosporine) (PBCS)

A solution of 1.0 mg. of staurosporine (2.15 micromoles) in 1.00 ml of dried ethyl acetate was treated with 45 microliters (1.08 micromoles) of a solution prepared from 3.83 mg of p-phylene diisocyanate (Trans World Chemicals P1586-1) in 1.00 ml of dried ethyl acetate. The reaction mixture was allowed to stand overnight. A white precipitate deposited. Then 0.5 ml of petroleum ether was added. The mixture was filtered into a vacuum-dried sintered-glass funnel. A total of 0.90 mg of crystalline product was collected and was identified as p-phenylene-bis-(carbamylstaurosporine) by fast atom bombardment mass spectroscopy.

$M+H^+$ Calculated=1093 Found=1093

Preparation A

N-Phenylcarbamylstaurosporine (PCS)

Reference: U.S. Pat. No. 5,093,330

A solution of 2.0 mg of staurosporine (4.30 micromoles) in 1.50 ml of dried ethyl acetate was treated with 468 μl (4.30 micromoles) of a solution of 10 μl of phenyl isocyanate in 0.990 ml of dried ethyl acetate. The solution was allowed to stand overnight and 3 ml of hexade was added in portions. Colorless crystals were obtained which weighed 2.39 mg. After recrystallizing this product from 1 ml of ethyl acetate and 2 ml of petroleum ether, 1.75 mg of a crystalline product was isolated. From a similar preparation, the product's composition as N-phenylcarbamylstaurosporine was verified by FAS-MS.

$M+H^+$ Calculated=586 Found=586

Preparation B

N-Phenylthiocarbamylstaurosporine (PTCS)

A solution of 1.0 mg (2.15 micromoles) of staurosporine in 1.00 ml of ethyl acetate was treated with 26 microliters of a stock solution of 10 microliters of phenyl isothiocyanate in 1.00 ml of ethyl acetate. This aliquot contained 290 micrograms (2.15 micromoles) of phenyl isothiocyanate. The reaction mixture was held at 25° C. overnight, and then 2.0 ml of hexade was added. The resulting crystalline product was filtered off, washed with hexade and dried with a stream of argon gas.

FAB-MS Calc: $M+H^+$=602 Found=602

Preparation C

N-Ethylcarbamylstaurosporine (ECS)

A solution of 0.9 mg (1.93 micromoles) of staurosporine in 900 microliters of ethyl acetate was treated with 1.93 micromoles (30.2 microliters of a stock solution of 9.05 mg of ethyl isocyanate in 2.00 ml of dried ethyl acetate) of ethyl isocyanate. The reaction mixture was held at 25° C. overnight, and 2.0 ml of hexade was added. The crystalline product was separated and dried.

| FAB-MS | Calc.: $M + H^+$ | = | 538 | $M + Na^+$ | = | 560 |
|---|---|---|---|---|---|---|
| | Found | = | 538 | | = | 560 |

EXAMPLE 3

Compound II-4

Compound A (962 mg, 2 mmol) was dissolved in a mixture of 30 ml of tetrahydrofuran and 10 ml of methanol, and then 760 mg of sodium borohydride (20 mmol) was added thereto under ice cooling, followed by stirring at the same temperature for 4 hours and further at room temperature for 12 hours. After 3N hydrochloric acid was added thereto, the solution was washed with an aqueous solution of sodium chloride and dried over magnesium sulfate, followed by evaporation of the solvent. The residue was purified by silica gel column chromatography (chloroform/methanol= 98/2) to give 882 mg (yield 97%) of Compound II-4.

Melting Point: 130°–140° C.

$^1$H-NMR (DMSO-d$_6$) δ (ppm): 2.032 (1H, dd, J=5.0, 13.9 Hz), 2.231 (3H, s), 2.967(3H, s), 3.609(1H, dd, J=7.6, 13.4 Hz), 3.959(2H, m), 5.000(2H, s), 5.268(1H, t, J=5.3 Hz ), 7.065 (1H, dd, J=4.9, 7.3 Hz), 7.254–8.038 (7H, m), 8.565(1H, s), 9.206(1H, d, J=7.8 Hz)

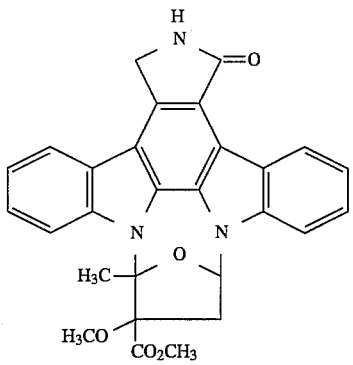

Compound A

EXAMPLE 4

Compound II-14

Compound B (393 mg, 0.9 mmol) was dissolved in 25 ml of tetrahydrofuran, and then 3 ml of tetrahydrofuran containing 309 mg of carbobenzoxy-L-serine (1.35 mmol), 156 mg of N-oxysuccinimide (1.35 mmol), 0.1 ml of 4-methylmorpholine (0.9 mmol) and 279 mg of dicyclohexylcarbodiimide (1.35 mmol) was added under ice cooling, followed by stirring for 12 hours. The reaction mixture was filtered and the solvent was evaporated. The residue was purified by silica gel column chromatography (chloroform/methanol= 99/1) to give 429 mg (yield 72%) of Compound C.

Melting Point: 188°–193° C.

SIMS (m/z): 660 $(M+1)^+$

Compound C (399 mg) was dissolved in 10 ml of dimethylformamide, and then 300 mg of 10% palladium on carbon was added, followed by stirring at 50° C. for 7 hours in a hydrogen stream. The reaction mixture was filtered through Celite and the solvent was evaporated. The residue was purified by silica gel column chromatography (chloroform/methanol/28% ammonium hydroxide=90/10/1) and the obtained product was dissolved in 5 ml of tetrahydrofuran, followed by addition of 5 ml of 1.7N hydrogen chloride/ethyl acetate and 10 ml of diethyl ether. The precipitate was separated from the solution by filtration to give 234 mg (yield 69%) of Compound II-14.

Melting Point: >300° C.

$^1$H-NMR (DMSO-d$_6$+D$_2$O) δ (ppm): 1.92–2.28(1H, m), 2.20 (3H, s), 2.84–3.12(7H, m), 3.40–4.20(5H, m), 5.04 (2H, s), 6.98(1H, m), 7.24–8.20(7H, m), 8.76(1H, brs), 9.22(1H, d, J=8 Hz)

SIMS (m/z ): 527 $(M+2)^+$

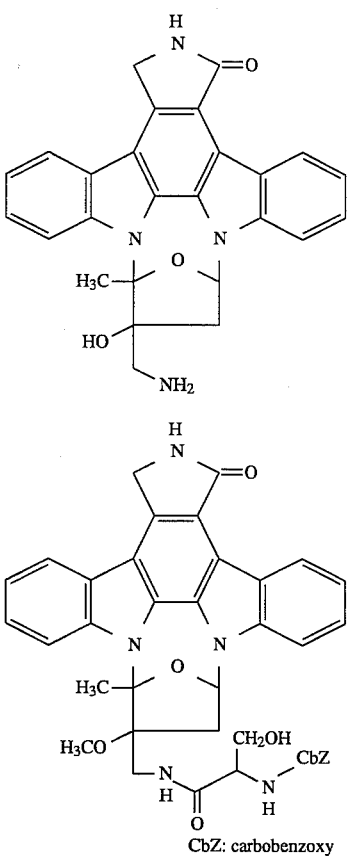

CbZ: carbobenzoxy

EXAMPLE 5

PC-12 cells are a clonal population arising from a tumor of rat adrenal medulla, and have proven to be an extremely useful and widely studied model for study of the actions of NGF (Guroff, Cell Culture in the Neurosciences, Plenum Publishing Corporation, 1985, Chapter 8, pages 245–272). One particularly robust effect of NGF on these cells is a rapid stimulation of the activity of ornithine decarboxylase (ODC), an effect which was reported to be blocked by 200 nM K-252a (Koizumi et al., 1988). In the experiments of this Example, PC-12 cells (obtained from Dr. G. Guroff) were cultured in 48-well plates at a density of $6 \times 10^4$ cells/cm$^2$ and incubated with drug vehicle (0.5% DMSO), staurosporine, or HBCS. K-252a and staurosporine are commercially available from Kamiya Biomedical. Four hours after drug addition, the cells were harvested for ODC assay, as described by Huff et al. (J. Cell Biol. 88: 189–198, 1981).

All three compounds produced an induction (i.e. increase) of ODC activity, but there were considerable differences in potency and efficacy (FIG. 1). K-252a produced a dose-dependent induction of ODC activity, with effects detectable at 2 nM and increasing to a maximum at 200 nM (36.3 fold induction). The effects of staurosporine were likewise detectable at 2 nM, but peaked at 20 nM (34.7 fold induction), and declined considerably at 200 nM. HBCS similarly induced at 2 nM, but higher concentrations failed to yield an increased effect, so that the maximum efficacy was much less than that of the other two compounds (6.5 fold induction). In another experiment, the effects of PTCS, PCS, and ECS on PC-12 cell ODC activity were compared to that of K-252a. At 200 nM concentrations, expressing the activity of K-252a as 100%, PTCS exhibited 71.4% of the activity of K-252a, while PCS and ECS exhibited 88.9% and 61.9% of the activity of K-252a, respectively. However, the protein kinase C inhibitor H-7 did not induce ODC activity at 30 μM, a concentration known to inhibit protein kinase C activity (Nakadate et al., Biochem. Pharmacol. 37: 1541–1545, 1988).

Figure 2:
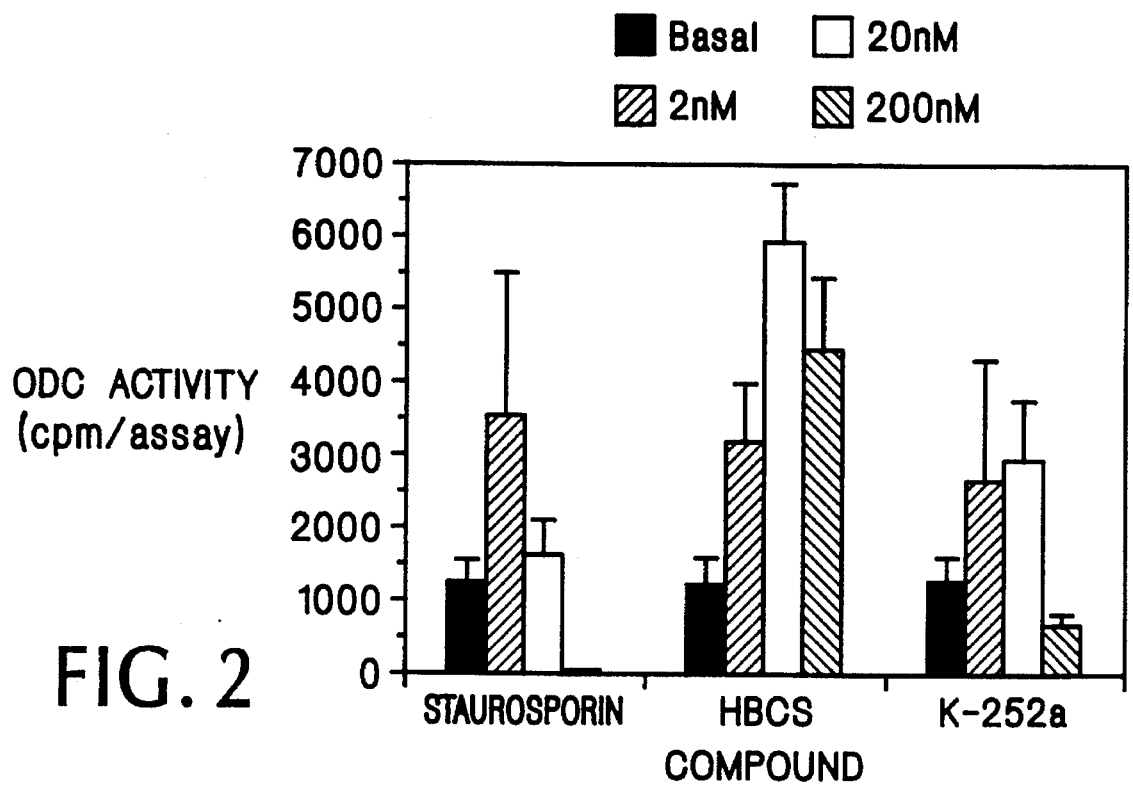
FIG. 2 is a graph illustrating the effects of staurosporine, HBCS, and K-252a on NGF-stimulated ODC activity in PC-12 cells.
Figure 3:
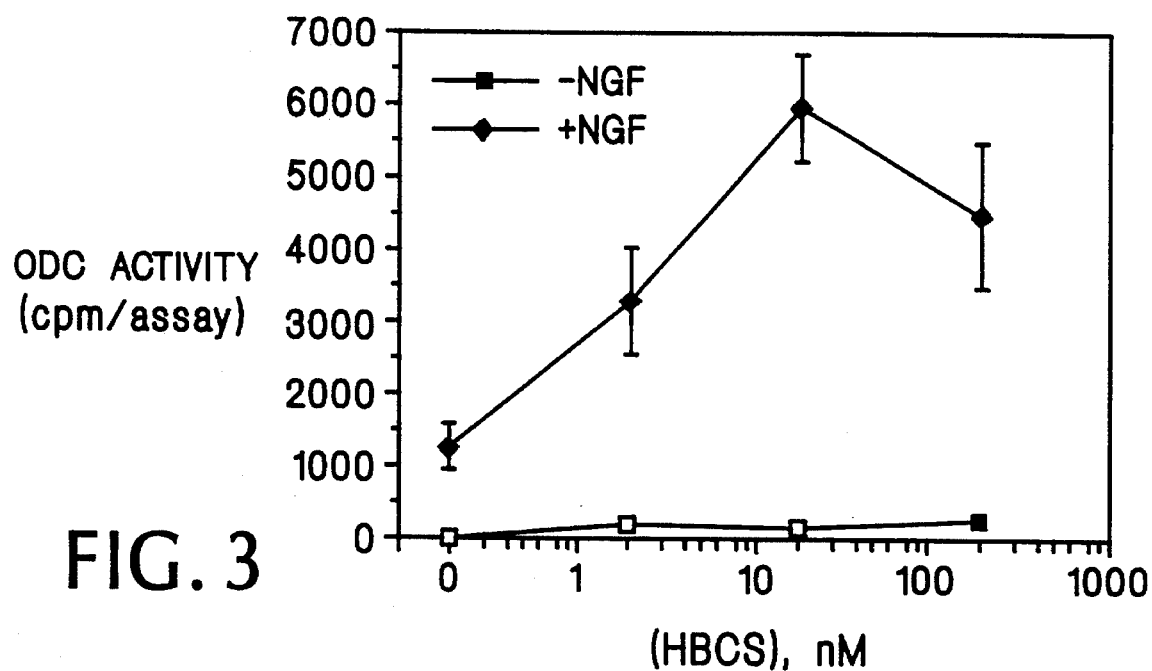
FIG. 3 is a graph illustrating the NGF-potentiating effect of HBCS on ODC activity in PC-12 cells.

The ability of K-252a, staurosporine and HBCS to potentiate and/or inhibit NGF bioactivity was assessed by adding 10 ng NGF per ml of cell culture medium, in the absence or presence of the above compounds in the concentrations previously indicated, followed by ODC assay of the cells as above (FIG. 2). This concentration of NGF was selected to provide an intermediate level of induction so that either potentiating or inhibiting effects of the compounds could be detected. K-252a at 200 nM inhibited the NGF induction of ODC, as reported by Koizumi et al. (1988), but, surprisingly, potentiated the induction at lower concentrations (2 nM and 20 nM). Staurosporine, at 2 nM, also potentiated the induction by NGF, but this effect was lost at higher concentrations (20 and 200 nM). HBCS, in contrast, potentiated the effects of NGF at all concentrations tested. This striking effect is shown relative to the modest ODC-inducing effects of HBCS alone in FIG. 3.

EXAMPLE 6

The effect of K-252a on choline acetyltransferase (ChAT) activity was assayed in dissociated spinal cord cultures prepared from fetal rats by standard methods (see below). ChAT is the enzyme that catalyzes the synthesis of the neurotransmitter acetylcholine, and is a specific biochemical marker for cholinergic neurons. In the spinal cord, the large majority of cholinergic neurons are motor neurons. Assay of this enzyme may thus be used as an indication of the effects of a factor (or factors) on the survival of cholinergic neurons and/or regulation of this enzyme.

Figure 4:
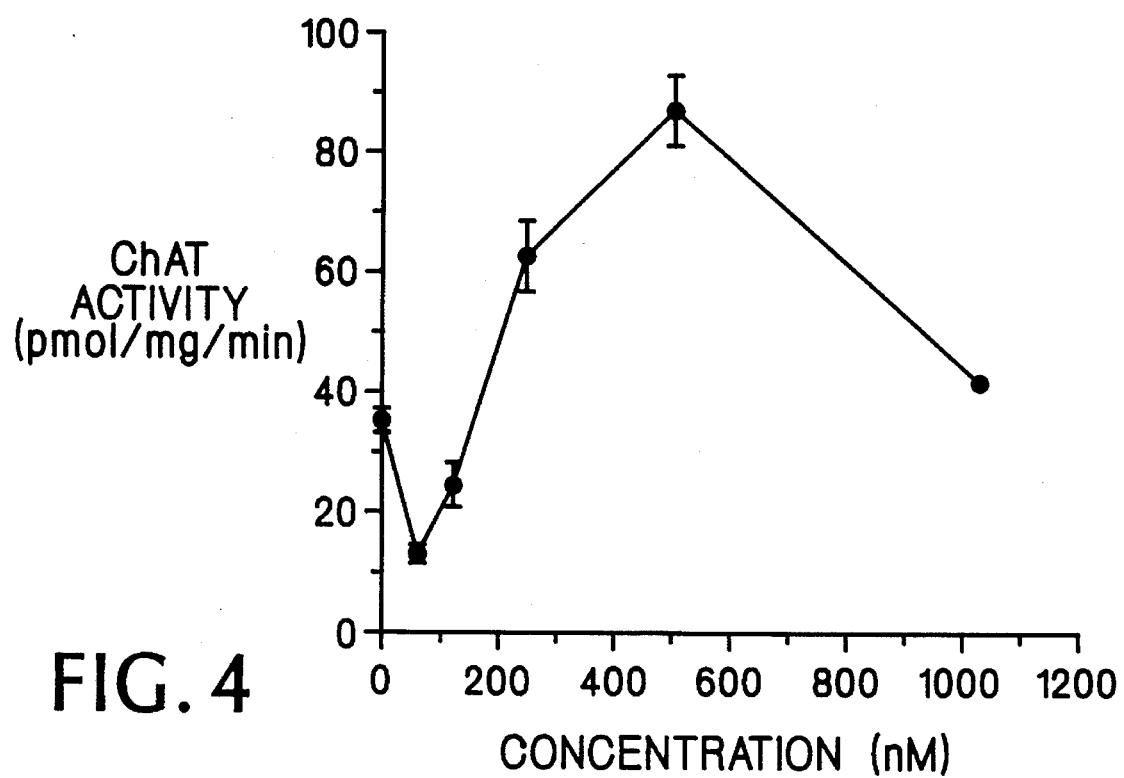
FIG. 4 is a graph illustrating the effect of K-252a on choline acetyltransferase (CHAT) specific activity in rat embryonic spinal cord cultures.
Figure 5:
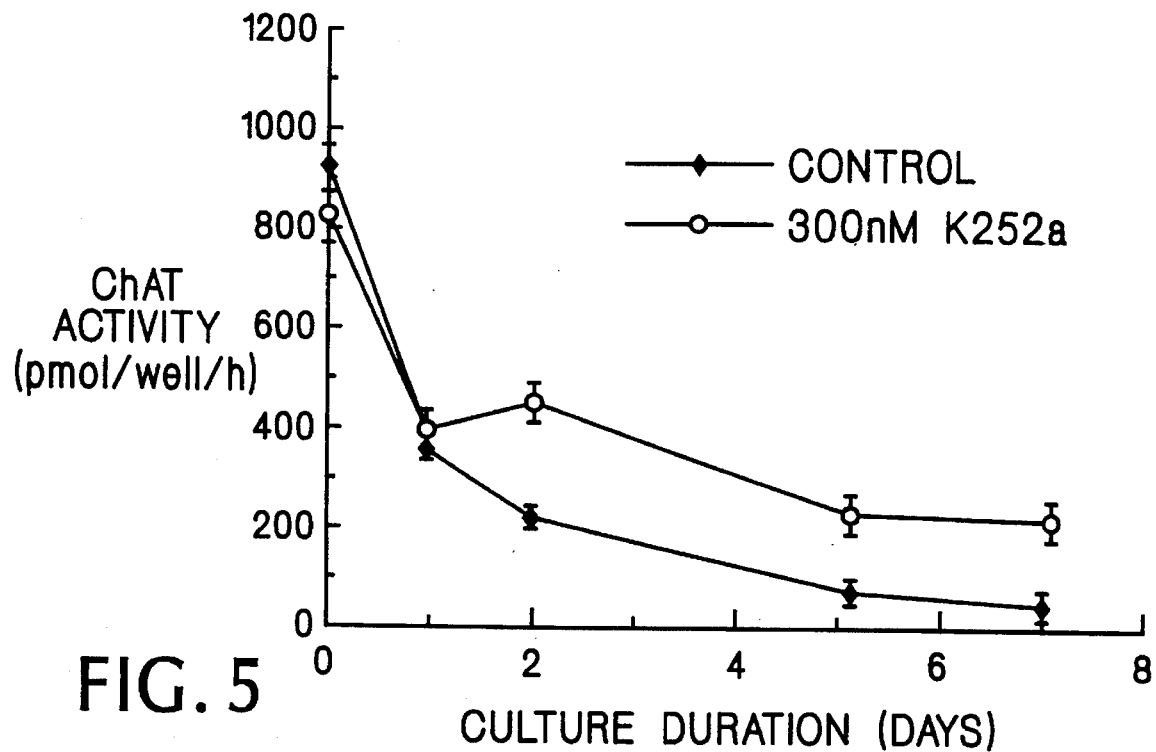
FIG. 5 is a graph illustrating the time course of K-252a effect on CHAT activity in rat embryonic spinal cord cultures.

K-252a was added at the indicated concentrations to the cultures after incubating 2–3 hours after plating to allow cells to attach to the substrate. ChAT activity was measured after 48 hours in culture. K-252a in spinal cord cultures resulted in a dose dependent increase in ChAT activity with maximum efficacy (2- to 3-fold increase) achieved at 200–300 nM (FIG. 4). Higher concentrations resulted in a decrease in ChAT activity (FIG. 4). Longer culture incubation times, up to seven days, resulted in 4- to-5 fold increases in ChAT activity (FIG. 5) due to the decreased basal level of ChAT activity. In this culture system, increasing numbers of motor neurons degenerate and die over time under basal (control) conditions (McManaman et al., Developmental Biol. 125: 311–320, 1988). The results shown in both FIGS. 4 and 5 are the result of a single application of K-252a on the day of culture initiation, indicating a prolonged effect on the survival of spinal cord cholinergic neurons and/or regulation of the enzyme itself. Methods: Experiments with dissociated cultures of fetal rat spinal cord cells were performed generally as described (Smith et al., J. Cell Biol. 101: 1608–1621, 1985). Dissociated cells were prepared from spinal cords dissected from day 14 embryonic rats by standard techniques known to those skilled in the art, using trypsin dissociation of tissue (Smith et al., 1985). Cells were seeded (plated) at $6 \times 10^5$ cells/cm$^2$ in poly-1-ornithine coated plastic tissue culture wells in serum-free N2 medium and incubated at 37° C. in a humidified atmosphere of 5% $CO_2$/95% air (Bottenstein and Sato, PNAS USA 76: 514–517, 1979) for 48 hours. ChAT activity was measured using modifications of the Fonnum procedure (J. Neurochem. 24: 407–409, 1975) according to Ishida and Deguchi (J. Neurosci. 3: 1818–1823, 1983), and McManaman et al., supra (1988). Activity was normalized to total protein measured by the bicinchonicic acid/$Cu^{++}$ reaction (BCA protein assay reagent, Pierce, Rockland, Ill.).

EXAMPLE 7

Figure 8:
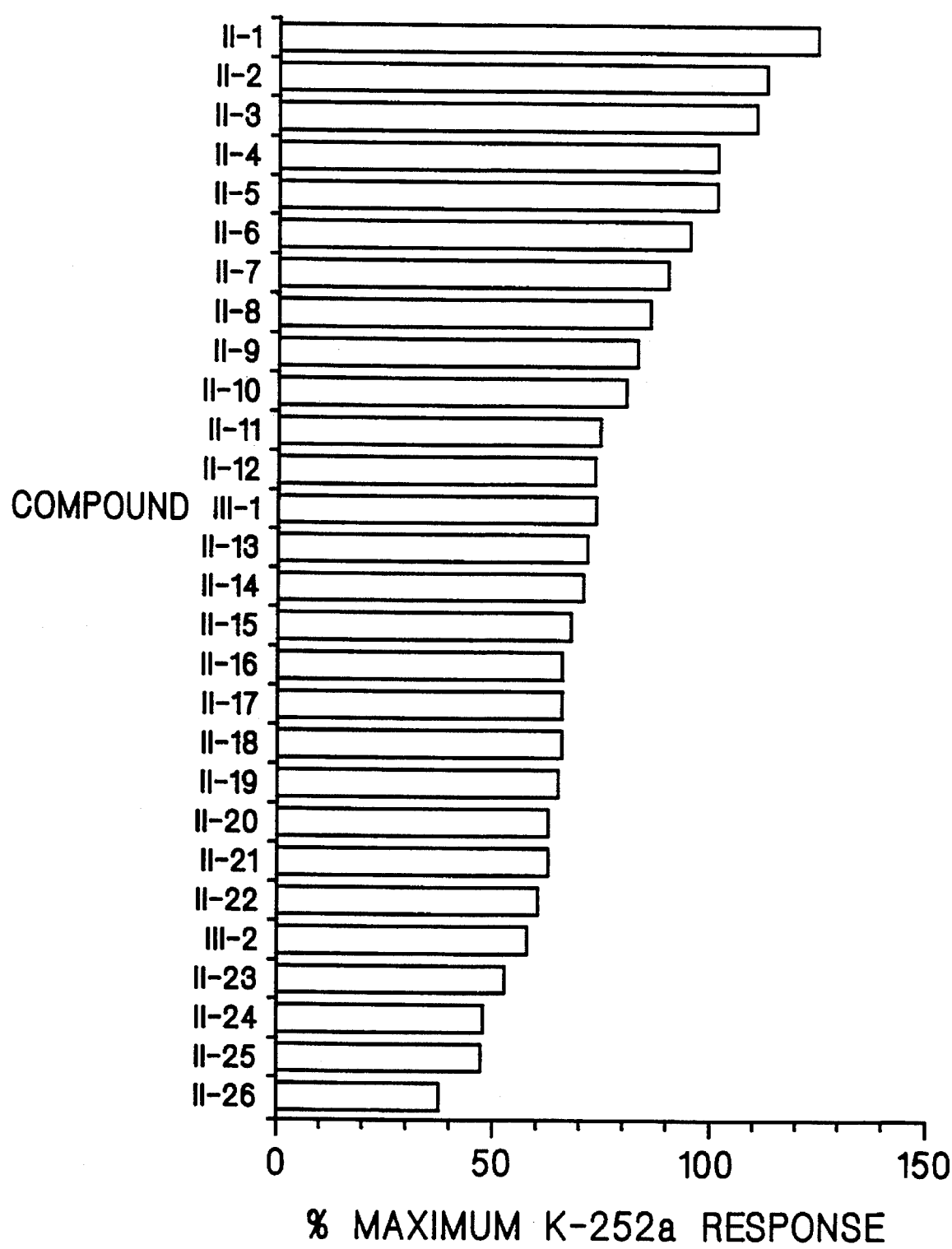
FIG. 8 is a graph illustrating the effect of K-252a functional derivatives on ChAT activity in rat embryonic spinal cord cultures.

Over one hundred functional derivatives of K-252a were tested in the spinal cord ChAT assay to determine their relative efficacy. The data shown in FIG. 8 show that out of the original functional derivatives tested at 300 and 30 nM, 28 resulted in significantly increased ChAT activity at 300 nM. One functional derivative, compound II-21, was also active at 30 nM (30% enhancement of ChAT activity over basal levels). This compound was more potent than K-252a or the remaining analogs since none of these actively enhanced ChAT activity at 30 nM.

FIG. 13 shows the effect of the original 28 K-252a derivatives shown to significantly increase ChAT activity in rat spinal cord cultures, as well as 30 additional derivatives (compounds II-29 through II-34, II-36 through II-56, and IV-1 through IV-3, all inclusive).

EXAMPLE 8

K-252a as well as 50 functional derivatives were assessed for their ability to promote dorsal root ganglion neuron cell survival. Cell survival was measured by uptake of calcein AM, an analog of the viable dye, fluorescein diacetate. Calcein is taken up by viable cells and cleaved intracellularly to fluorescent salts which are retained by intact membranes of viable cells. Microscopic counts of viable neurons correlate directly with relative fluorescence values obtained with the fluorimetric viability assay. This method thus provides a reliable and quantitive measurement of cell survival in the total cell population of a given culture.

Figure 6:
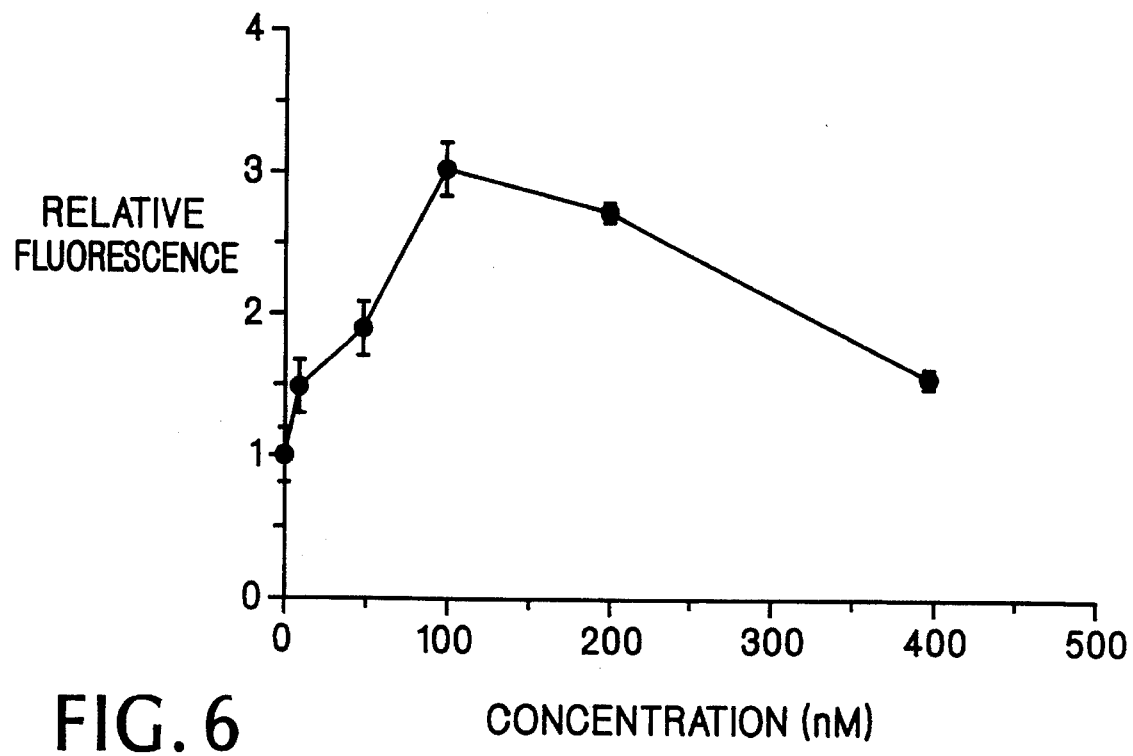
FIG. 6 is a graph illustrating the effect of K-252a on survival of chick embryonic dorsal root ganglion neurons.
Figure 7:
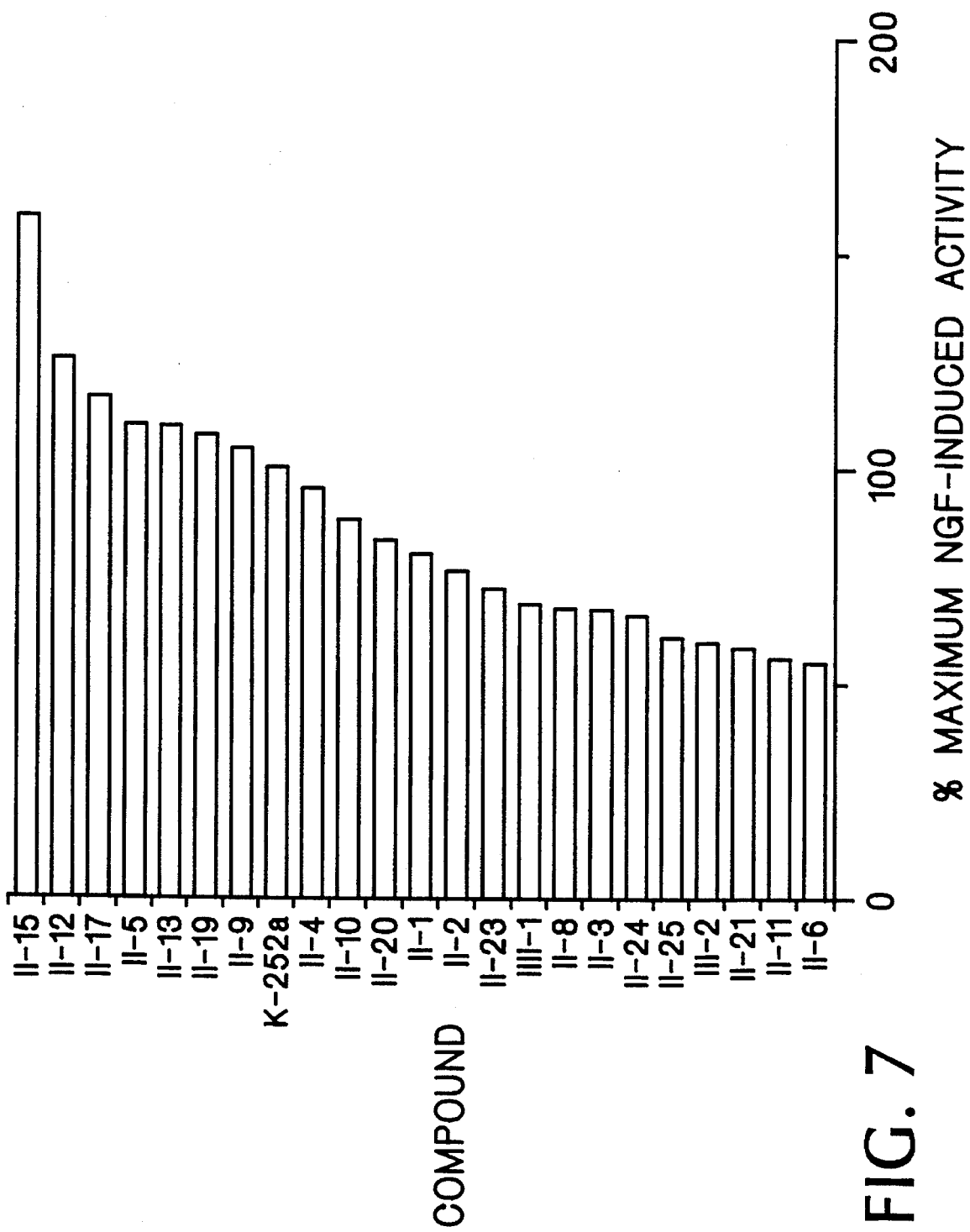
FIG. 7 is a graph illustrating the effect of K-252a functional derivatives on survival of chick embryonic dorsal root ganglion neurons.

Dorsal root ganglion neuron survival was enhanced by K-252a in a concentration-dependent manner; maximum activity was observed at approximately 100 nM (FIG. 6). Twenty-four of the 50 analogs tested were active in promoting DRG neuron survival, twenty-two of which are shown in FIG. 7. All of these analogs were also active in increasing spinal cord ChAT activity (see Example 5, FIG. 8). The original 22 as well as the 2 additional active analogs (II-30, II-32) are shown in FIG. 14. Microscopic examination of the dorsal root ganglion neurons stimulated with the twenty-four active functional derivatives indicated enhanced nerve fiber outgrowth as well.

Methods: Dorsal root ganglia were dissected from embryonic age day 8 chick embryos and dissociated cells prepared by subsequent Dispase (neutral protease, Collaborative Research) dissociation. Neurons were seeded at low density ($1.8 \times 10^4$ cells/$cm^2$) into 96 well poly-L-ornithine and laminin coated plates. Cells were cultured for 48 hours in serum-free N2 medium (Bottenstein and Sato, 1979) at 37° C. in a humidified atmosphere, 5% $Co_2$/95% air. Cell survival was assessed at 48 hours using the viable fluorimetric assay described above.

EXAMPLE 9

Infusion of the excitatory amino acid kainic acid (kainate) directly into the ventricles of a rodent brain results in neuronal degeneration of the pyramidal cells of the hippocampus. This neuronal death is characterized by a marked increase in the proteolysis of the cytoskeletal protein, spectrin. Spectrin breakdown products can be measured in homogenates of the hippocampus within 24 hours following kainate administration. The magnitude of spectrin proteolysis is highly correlated with the magnitude of neuronal death in pyramidal cells of the hippocampus (Siman et al., J. Neurosci. 9: 1579–1590, 1989), and thus spectrin proteolysis is an excellent biochemical marker of excitatory amino acid-induced neuronal degeneration. Excessive release of endogenous excitatory amino acids has been implicated as an etiology in numerous neurological diseases and disorders, including stroke and other ischemic injuries; Alzheimer's disease; motor neuron disease including amyotrophic lateral sclerosis; Parkinson's disease; Huntington's disease; AIDS dementia; epilepsy; and concussive or penetrating injuries of the brain or spinal cord.

Figure 9:
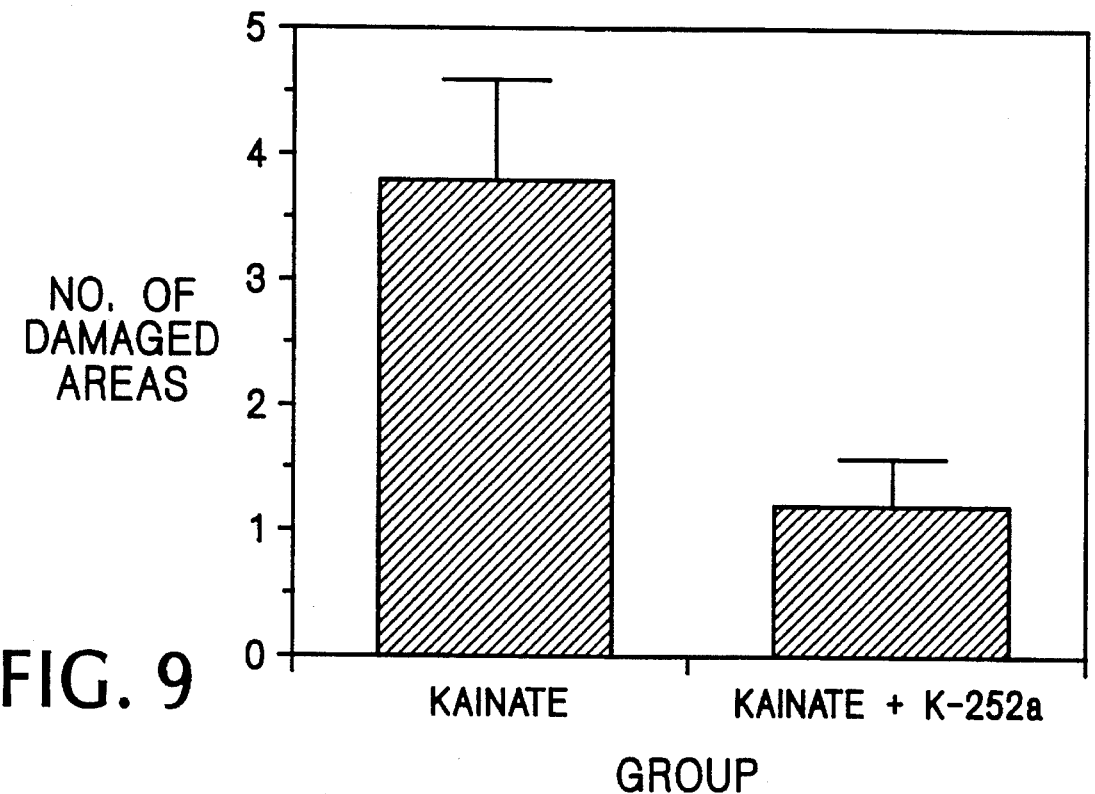
FIG. 9 is a graph illustrating the effect of K-252a on kainate-induced damage to the rat hippocampus.

FIG. 9 shows the effect of K-252a on kainate-induced neuronal degeneration in the hippocampus. Cannulated male and female Sprague-Dawley rats received 0.4 µg of K-252a, or vehicle, 30 minutes prior to and about 3 and 24 hours following kainate (0.6 µg) injection directly into the lateral cerebral ventricles of the brain (icv). Two weeks later the brains were excised, frozen, sectioned and stained for histological analysis, as described below. Data shown are the mean number of sub-regions of the hippocampus damaged for each group, ±S.E.M. K-252a significantly reduced the number of damaged areas within the hippocampus from 3.86±0.78 (in the absence of K-252a) to 1.18±0.4 (in the presence of K-252a).

Figure 10:
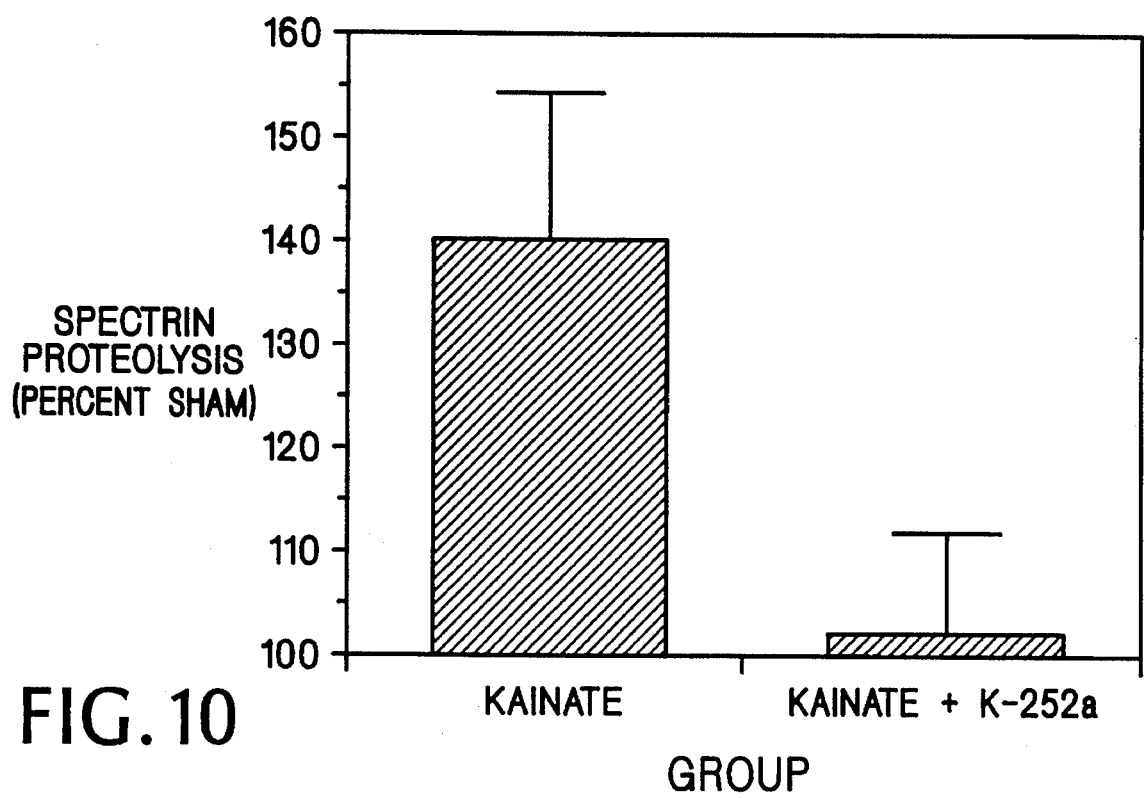
FIG. 10 is a graph illustrating the effect of K-252a on kainate-induced spectrin proteolysis in the rat hippocampus.

FIG. 10 shows the effect of K-252a on kainate-induced spectrin breakdown in the hippocampus. Female Sprague-Dawley rats received 0.4 µg of K-252a, or vehicle, together with a neurotoxic dose of kainate (0.6 µg), by icv infusion. Sham control animals received infusions of vehicle, but no kainate or K-252a. Twenty-four hours later, homogenates of the dorsal hippocampus were analyzed for spectrin breakdown products as described below. The magnitude of spectrin proteolysis is expressed as a percent increase in spectrin breakdown products for each group over sham control values. Data shown are the mean percent increase in spectrin breakdown products for each group (sham=100%)±S.E.M. Icv infusion of K-252a significantly reduced the extent of spectrin proteolysis, from about 140±15% (in the absence of K-252a) to approximately 102±10% (in the presence of K-252a) of sham values.

EXAMPLE 10

Figure 11:
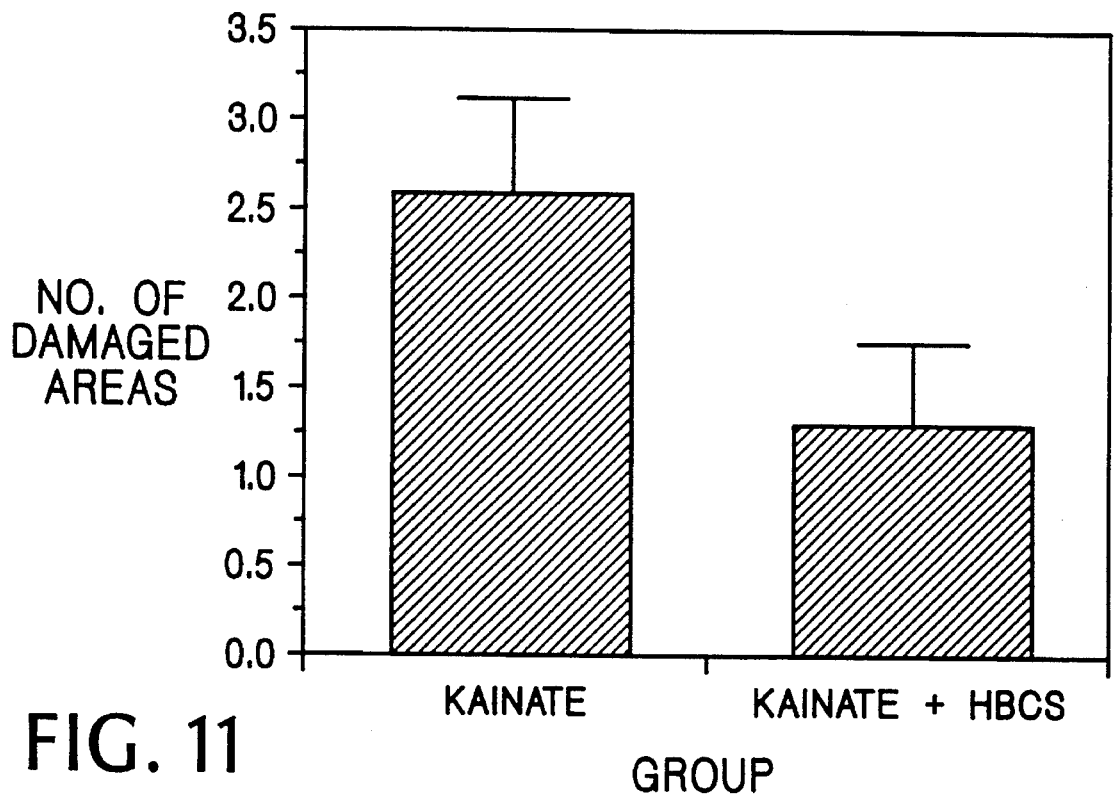
FIG. 11 is a graph illustrating the effect of HBCS on kainate-induced damage to the hippocampus.

FIG. 11 shows the effect of HBCS on kainate-induced neuronal degeneration in the hippocampus. Cannulated female Sprague-Dawley rats received 0.8 µg of HBCS, or vehicle, 40 minutes prior to and about 4 hours following kainate (0.6 µg) by icv infusion. Two weeks later the brains were excised, frozen, sectioned and stained for histological analysis, as described below. Data shown are the mean number of sub-regions of the hippocampus damaged for each group, ±S.E.M. HBCS significantly reduced the number of damaged areas within the hippocampus from about 2.5±0.6 (without HBCS treatment) to 1.3±0.5 (with HBCS treatment).

EXAMPLE 11

Figure 12:
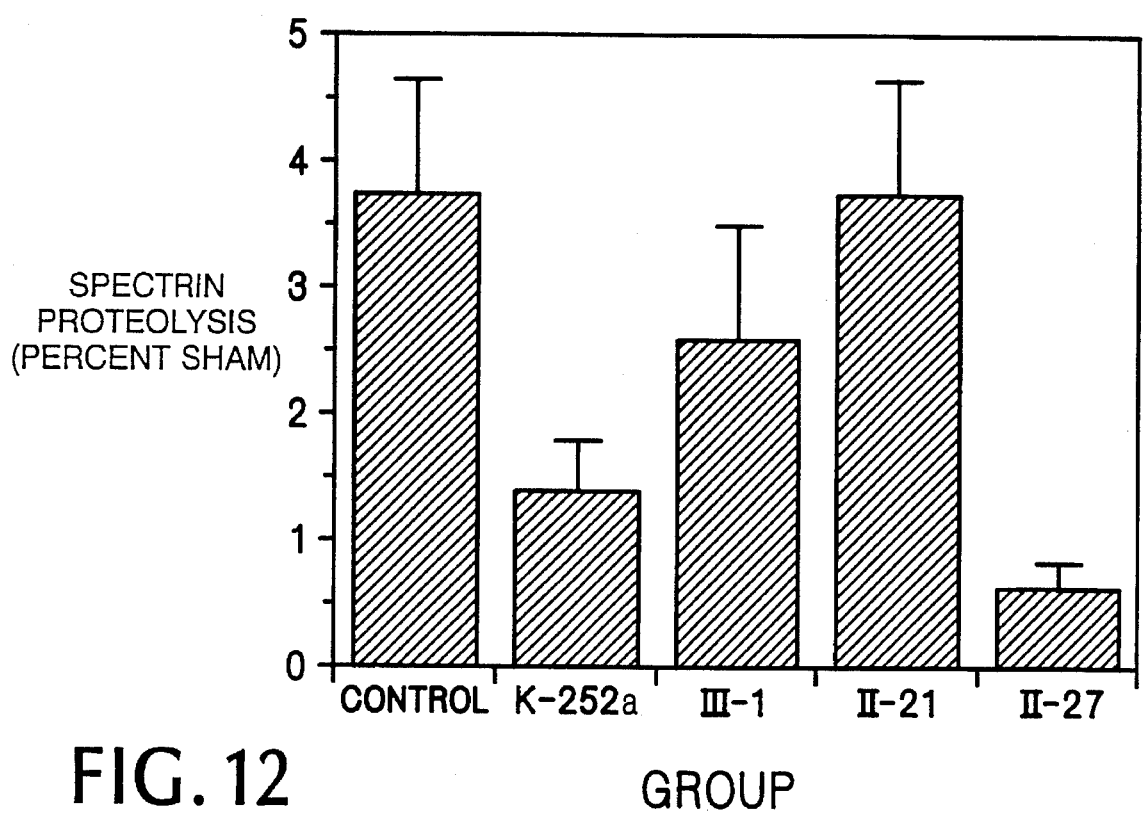
FIG. 12 is a graph illustrating the effect of K-252a analogs on kainate-induced spectrin proteolysis in the rat hippocampus.

FIG. 12 compares the effect of three K-252a functional derivatives on kainate-induced spectrin breakdown in the hippocampus. Female Sprague-Dawley rats received 0.4 µg of K-252a, or compounds III-1, or II-21, or vehicle, together with a neurotoxic dose of kainate (0.6 µg), by icv infusion. Sham control animals received infusions of vehicle, but no kainate or K-252a derivative. Twenty-four hours later, homogenates of the dorsal hippocampus were analyzed for spectrin breakdown products as described below. The magnitude of spectrin proteolysis is expressed as a percent increase in spectrin breakdown products for each group over sham control values. Data shown are the mean percent increase in spectrin breakdown products for each group (sham=100%)±S.E.M. Icv infusion of K-252a reduced the extent of spectrin proteolysis, from about 128+9% (vehicle treatment) to approximately 104±4% (in the presence of K-252a) of sham values. The K-252a derivatives, III-1 and II-21, failed to prevent kainate-induced spectrin proteolysis.

Methods of FIGS. 9–12

Kainate infusion regime:

The effect of K-252a or its derivatives on kainate-induced neuronal damage was evaluated as follows: Adult male or female Sprague-Dawley rats (175–250 g) were anesthetized with Nembutal (50 mg/kg, ip) and administered a drug, or vehicle treatment, in a total of 5 μl, before and after kainate treatment (5 μl) by icv infusion using a dose and infusion schedule as indicated for individual cases above. Control animals received vehicle instead of kainate and drug infusion. For anatomical studies, icv infusions were delivered through a cannula (Plastic One, Roanoke, Va.) implanted approximately one week before drug infusions, and positioned at stereotaxic coordinates: anterior-posterior at bregma, 1.5 mm lateral to bregma, and 4.4 mm ventral from the top of the skull. Results of this treatment regimen were evaluated two weeks later using the anatomical analysis described below.

In studies to assess the effect of K-252a or its derivatives on kainate-induced spectrin proteolysis, anesthetized rats received a 5 μl icv infusion of the drug, or vehicle, simultaneously with kainate, through a 10 μl Hamilton syringe positioned at the stereotaxic coordinates described above. These rats were killed 24 hours later and subjected to biochemical analysis as described below.

Anatomical and Biochemical Analyses

Anatomical analysis was performed as follows. Rats were killed by decapitation 2 weeks following treatments, and the brains were rapidly removed and frozen on dry ice. A series of slide-mounted coronal sections from each brain was stained with thionin and examined microscopically. Damage to the hippocampus was quantified by summing the total number of 4 anatomically defined regions of the hippocampus (CA1–4 according to the classification of Lorente de No, as described by Shepard, 1979, *The Synaptic Organization of the Brain*, Oxford, p. 310, hereby incorporated by reference), on both left and right sides of the brain, that suffered a loss of pyramidal cells.

Biochemical analysis was performed as follows. Calpain I-sensitive proteolysis of brain spectrin (fodrin) was evaluated in homogenates of the hippocampus using an immunoblot analysis described by Siman et al. (1988, Neuron, 1: 279–287, hereby incorporated by reference). Briefly, rats were killed by decapitation 24 hours following treatment, and the dorsal hippocampus was rapidly dissected out of the brain and homogenized in 20 mM Tris-HCl (pH 7.4) containing 0.1 mM phenylmethylsulfonyl fluoride. Proteins from aliquots of each homogenate were separated by SDS-PAGE, and an immunoblot analysis was used to quantitate the amount of kainate-induced spectrin breakdown in each sample.

EXAMPLE 12

K-252a was assessed for its ability to promote survival in striatal cultures. Striata were dissected from embryonic day 17 rat embryos and cells were dissociated by Dispase (neutral protease, Collaborative Research). Neurons were seeded at $5 \times 10^4$/well ($1.5 \times 10^5$/cm$^2$) in 96-well plates onto wells previously coated with poly-1-ornithine and laminin. Cells were cultured in serum-free N2 medium containing 0.05% bovine serum albumin (Bottenstein and Sato, 1979) at 37° C. in a humidified atmosphere, 5% $CO_2$/95% air. Cell survival was assessed 5 days after seeding using the calcein viable fluorimetric assay described in Example 8.

Figure 15:
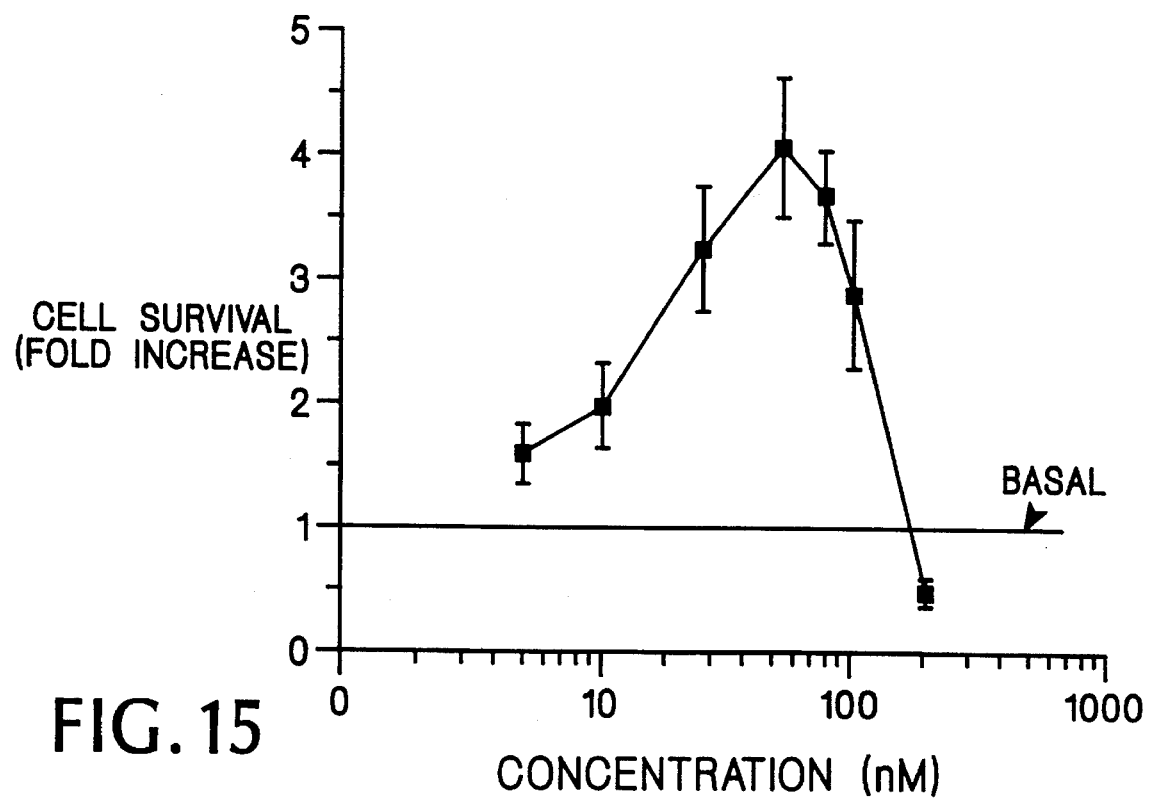
Figure 16:
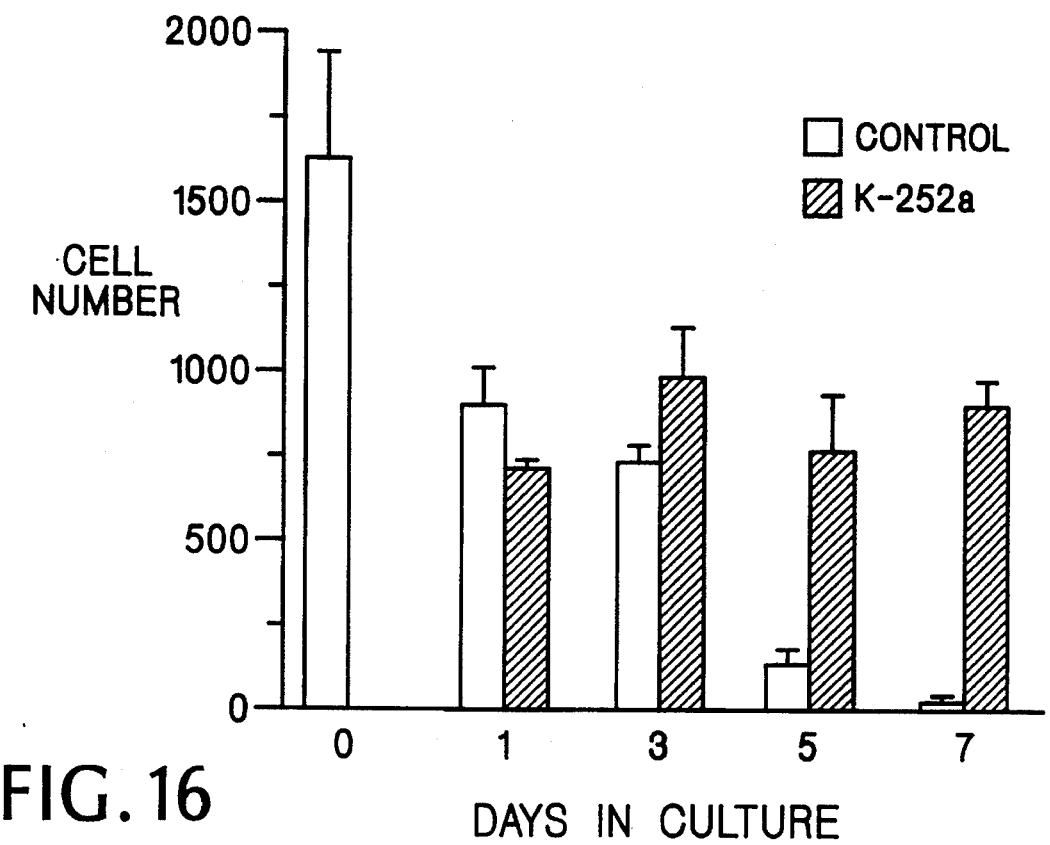

Striatal neuronal survival was enhanced by K-252a in a concentration-dependent manner. Maximum activity was found with 75 nM K-252a, and produced an efficacy of 3–4 fold over control (FIG. 15). In the control cultures, 90% of the neurons plated on day 0 died within 5 days, whereas in cultures treated with K-252a, 50% of the neurons survived (FIG. 16). The survival effect in striatal neurons occurred after 3 days in culture and was sustained for at least 7 days in culture. These results are from a single application of K-252a on the day of culture initiation indicating a sustained effect of survival on a certain population of neurons.

Figure 17:
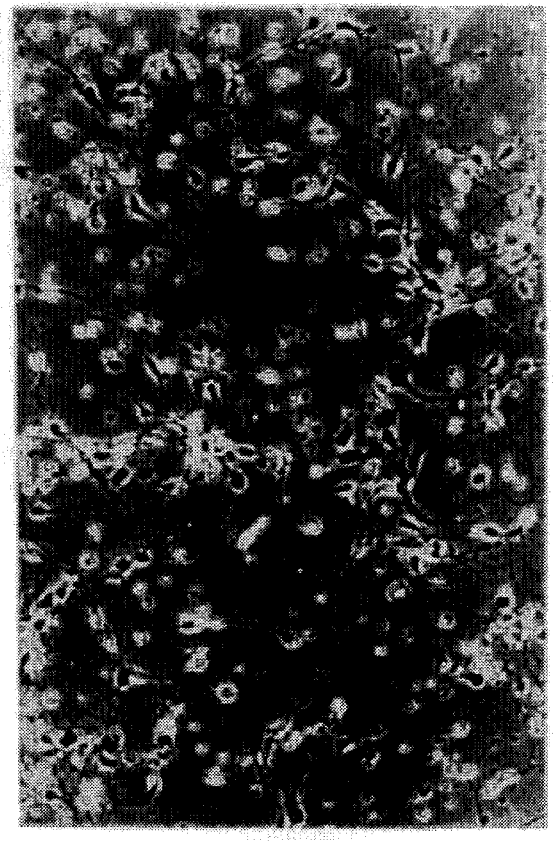
Figure 17:
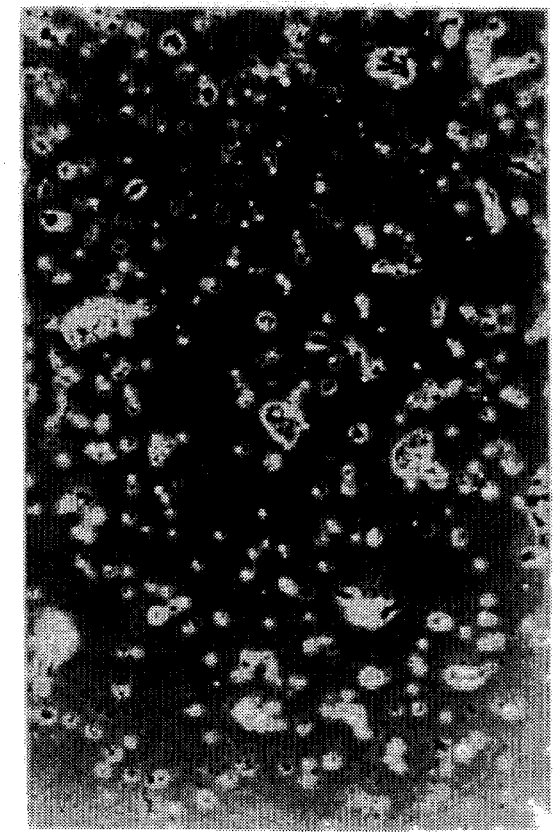

FIG. 17 is a pair of photomicrographs taken from control cultures or cultures treated with 75 nM K-252a. There was an increase in cell survival and neurite outgrowth in these cultures in the presence of 75 nM K-252a.

EXAMPLE 13

Thirty-one functional derivatives of K-252a were tested to determine their potency and efficacy in the striatal cell survival assay of Example 10. FIG. 18 shows data on 18 K-252a derivatives that promoted the survival of striatal neurons.

Processes for Producing Compounds (V)

The processes for producing Compounds (V) are described below.

Process 1

Compound (V-1) [Compound V in which $R^1$ is $CH_2SO_2R^7$ and X is $CO_2R^5$] can be prepared by the following reaction step:

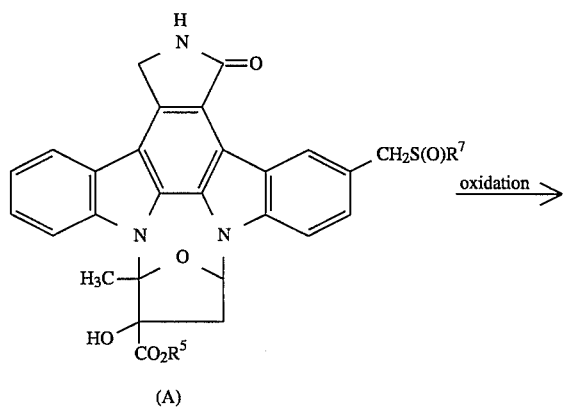

(A)

-continued

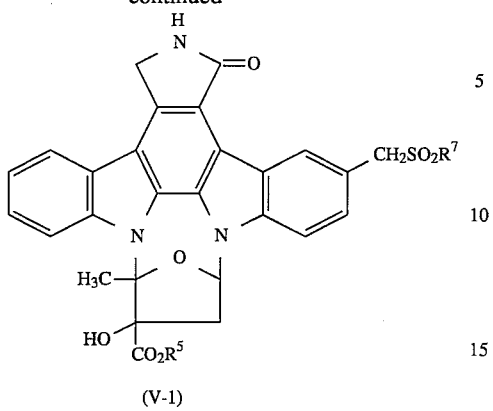

(V-1)

($R^5$ represents lower alkyl or $CH_2NHCO_2R^6$ in which $R^6$ represents lower alkyl or aryl; $R^7$ represents lower alkyl.)

The starting compound (A) is disclosed in Japanese Published Unexamined Patent Application No. 295588/88 (hereby incorporated by reference).

Compound (V-1) can be obtained by treatment of Compound (A) with 1 to 1.5 equivalents of an oxidant. An example of the oxidant is m-chloroperbenzoic acid. As a reaction solvent, a halogenated hydrocarbon such as methylene chloride, chloroform, or ethylene dichloride, or the like is used. The reaction is completed in 0.5 to 1 hour at −20° to 30° C.

Process 2

Compounds (V-2) [Compound (V) in which $R^1$ is hydrogen and X is $CH_2NHCO_2R^6$] can be prepared by the following reaction step:

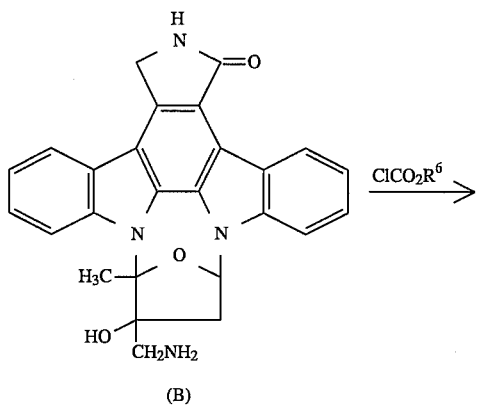

-continued (V-2)

$R^6$ represents lower alkyl or aryl.

The starting compound (B) is disclosed in Japanese Published Unexamined Patent Application No. 155285/87 (hereby incorporated by reference).

Compound (V-2) can be obtained by reaction of Compound (B) with 1 to 3 equivalents $ClCO_2R^6$ in the presence of 1 to 3 equivlents of a base. An example of the base is triethylamine. As a reaction solvent, a halogenated hydrocarbon such as methylene chloride, chloroform, or ethylene dichloride, or the like is used. The reaction is completed in 0.5 to 3 hours at −10° to 30° C.

EXAMPLE 14

Compound II-49

Compound (A-1; $R^5=CH_3$ and $R^7=C_2H_5$) (27 mg, 0.05 mmol) was dissolved in 1 ml of chloroform, and then 10 mg (0.06 mmol) of m-chloroperbenzoic acid was added thereto under ice cooling, followed by stirring at the same temperature for 45 minutes. After dilution with chloroform, the mixture was washed successively with a 8% aqueous solution of sodium thiosulfate, a saturated aqueous solution of sodium bicarbonate, water, and a saline solution, and dried over sodium sulfate. After evaporation of the solvent, the residue was subjected to silica gel column chromatography (chloroform/methanol=95/5) to give 17.7 mg (yield 62%) of Compound II-49.

$^1$H-NMR (DMSO-$d_6$) δ (ppm): 1.298(3H, t, J=7.5 Hz), 2.037 (1H, dd, J-5.0, 14.1 Hz), 2.153(3H, s), 3.096(2H, q, J=7.5 Hz), 3.266 (2H, s), 3,929(3H, s), 4.985 (1H, d, J=17.0 Hz), 5.043(1H, d, J=17.0 Hz), 6.348(1H, s), 7.147 (1H, dd, J=4.9, 7.1 Hz), 7.345–8.070(6H, m), 8.612(1H, s), 9.232(1H, d, J=1.5 Hz)

FAB-MS (m/z): 574 (M+1)$^+$

EXAMPLE 15

Compound II-57

Compound (B) (43.8 mg, 0.1 mmol) was dissolved in 1 ml of tetrahydrofuran, and then 9.3 μl (0.12 mmol) methyl chloroformate and 28 μl(0.2 mmol) of triethylamine were added thereto, followed by stirring for 50 minutes under ice cooling. After dilution with tetrahydrofuran, the mixture was washed with a saline solution, and dried over sodium sulfate. After evaporation of the solvent, the residue was subjected to silica gel column chromatography (chloroform/methanol=99/1) to give 32.6 mg of Compound II-57.

$^1$H-NMR (CDCl$_3$) δ (ppm): 2.099(3H, s), 2.679(1H, m), 3.204(1H, dd, J=6.7m 13.8 Hz), 3.837(3H, s), 4.446 (1H, d, J=17.3 Hz), 4,634 (1H, d, J=17.6 Hz), 5.497 (1H, brs), 6.591(1H, brs), 7.010–8.037(7H, m), 8.592(1H, d, J=6.6 Hz)

FAB-MS (m/z): 497 (M+1)$^+$

EXAMPLE 16

Compound II-38

Substantially the same procedure as in Example 15 was repeated using 43.8 mg (0.1 mmol) of Compound (B) and 15 μl of phenyl chloroformate to give 27.8 mg (yield 50%) of Compound II-38.

$^1$H-NMR (CDCl$_3$) δ (ppm): 2.111(3H, s), 2.890(1H, brd, J=13.7 Hz), 3.262(1H, dd, J=7.5, 13.9 Hz), 3.742 (1H, d, J=13.4 Hz), 3.967(1H, d, J=12.9 Hz), 4.582(1H, d, J=16.3 Hz), 5.342(1H, brs), 5.906(1H, brs), 6.550 (1H, brs), 7.005–8.042(12H, m), 8.596(1H, d, J=7.6 Hz)

FAB-MS (m/z): 559 (M+1)$^+$

EXAMPLE 17

Figure 19:
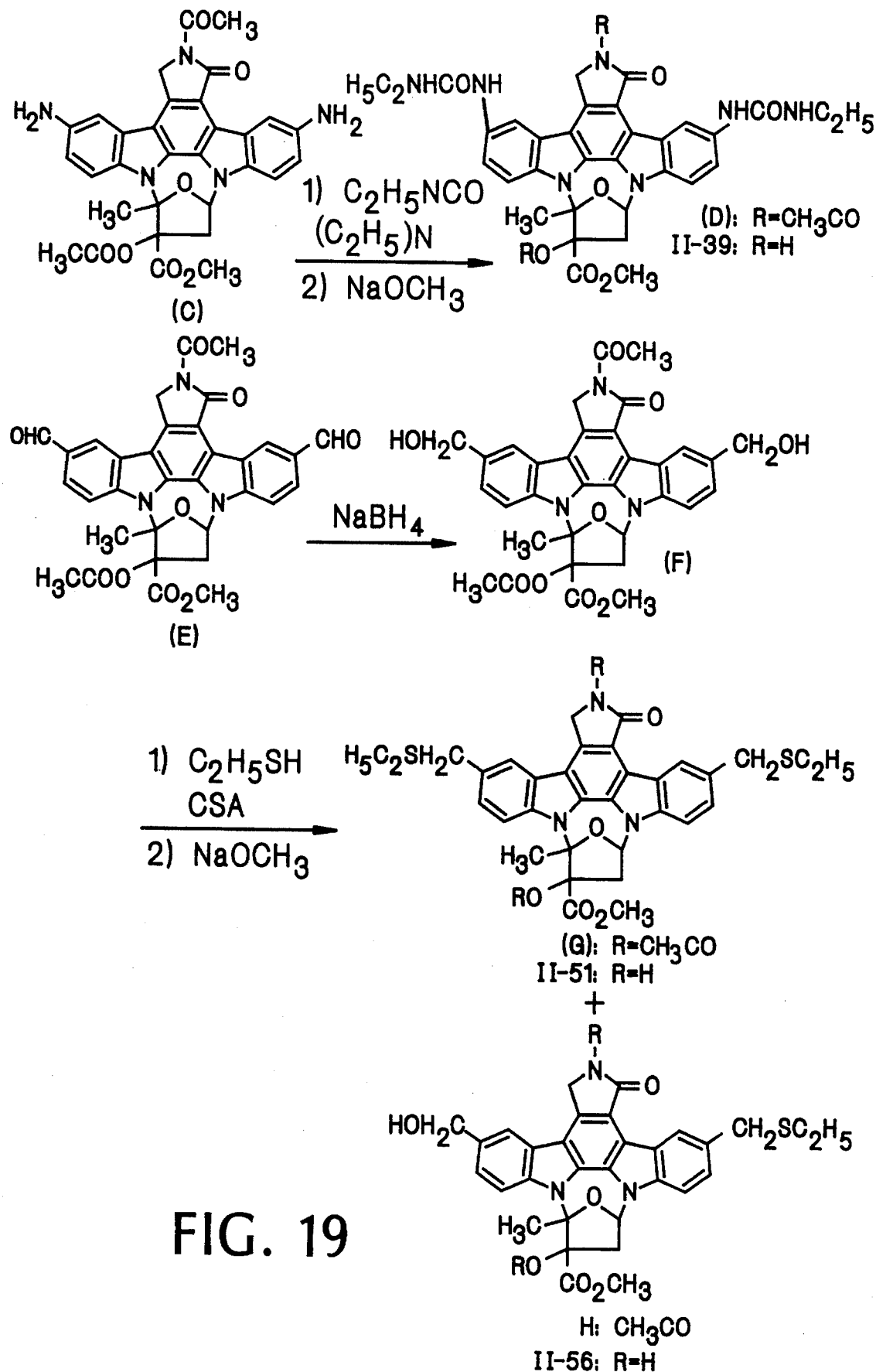
FIG. 19 shows the synthesis of Compound H from starting Compound C.

(The synthesis of Compound H from Compound C is shown in FIG. 19.)

Compound II-39

Compound (C) (Japanese Published Unexamined Patent Application No. 295588/88; hereby incorporated by reference) (20 mg, 0.035 mmol) was dissolved in 1 ml of chloroform, and then 14.6 μl (0.105 mmol) of triethylamine and 13.9 μl (0.175 mmol) of ethyl isocyanate were added thereto, followed by stirring at room temperature for 2 hours. To the solution was added 1 ml of methanol, followed by dilution with chloroform. The mixture was washed successively with water and a saline solution, and dried over sodium sulfate. After evaporation of the solvent, the residue was subjected to silica gel column chromatography (chloroform/methanol=98/2) to give 21 mg (yield 84% of Compound (D).

$^1$H-NMR (CDCl$_3$) δ (ppm): 1.195(3H, t, J=7.2 Hz), 1.222(3H, t, J=7.2 Hz), 1.664(3H, s), 2.194(3H, s), 2.555(3H, s), 3.346(4H, q, J=7.2 Hz), 3.820(1H, dd, J=7.5, 14.6 Hz), 3.938(3H, s), 5.036(1H, d, J=17.7 Hz), 5.125(1H, d, J=17.2 Hz), 6.745(1H, dd, J=4.8, 7.4 Hz), 7.260–7.898(5H, m), 8.690(1H, d, J=1.9 Hz)

FAB-MS (m/z): 724 (M+1)$^+$

Compound (D) (9 mg, 0.012 mmol) was dissolved in a mixture of 0.2 ml of tetrahydrofuran and 0.2 ml of methanol, and then 2 μl of 28% sodium methoxide/methanol was added thereto, followed by stirring at room temperature for minutes. To the solution was added 0.1 ml of a 5% aqueous solution of citric acid, followed by dilution with chloroform. The mixture was washed successively with water and a saline solution, and dried over sodium sulfate. After evaporation of the solvent, the residue was subjected to silica gel column chromatography (chloroform/methanol=9/1) to give 8 mg of Compound II-39.

$^1$H-NMR (DMSO-d$_6$) δ (ppm): 1.086(3H, t, J=7.1 Hz), 1.099 (3H, t, J=7.1 Hz), 1.948(1H, dd, J=4.8, 14.1 Hz), 2.107(3H, s), 3.158(4H, m), 3.910(3H, s), 4.880(1H, d, J=17.7 Hz), 4.931(1H, d, J=16.9 Hz), 7.028(1H, dd, J=5.0, 7.1 Hz), 7.332–8.287(5H, m), 8.838(1H, d, J=2.1 Hz)

FAB-MS (m/z): 640 (M+1)$^+$

EXAMPLE 18

Compounds II-51 and II-56

Compound (E) (Japanese Published Unexamined Patent Application No. 295588/88; supra) (60.7 mg, 0.1 mmol) was dissolved in a mixture of 5 ml of chloroform and 1 ml of methanol, and then 11 mg (0.3 mmol) of sodium borohydride was added thereto under ice cooling, followed by stirring at the same temperature for 15 minutes. After dilution with chloroform, the mixture was washed successively with water and a saline solution, and dried over potassium carbonate. After evaporation of the solvent, the residue was subjected to silica gel column chromatography (Chloroform/methanol/triethylamine=98/2/0.5) to give 36 mg (yield 59%) of Compound (F).

$^1$H-NMR (DMSO-d$_6$) δ (ppm): 1.650(3H, s), 2.027 (1H, dd, J=4.9, 14.5 Hz), 2.126(3H, s), 3.843(1H, dd, J=7.4, 14.5 Hz), 3.891(3H, s), 4.607(2H, s), 4.673(2H, s), 5.125(2H, s), 7.099(1H, dd, J=5.0, 7.3 Hz), 7.437–7.907(5H, m), 8.812(1H, d, J=0.8 Hz)

FAB-MS (m/z): 612 (M+1)$^+$

Compound (F) (159 mg, 0.26 mmol) was dissolved in 15 ml of chloroform, and then 0.8 ml (10.4 mmol) of ethanethiol and 24 mg (0.104 mmol) of camphorsulfonic acid were added thereto, followed by stirring at room temperature for 12 hours. The solution was washed successively with a saturated aqueous solution of sodium bicarbonate, water, and a saline solution, and dried over sodium sulfate. After evaporation of the solvent, the residue was subjected to silica gel column chromatography (ethyl acetate/toluene=1/9–chloroform/methanol=99/1) to give 43 mg of Compound (G) and 75 mg of Compound (H).

Compound (G)

$^1$H-NMR (CDCl$_3$) δ (ppm): 1.292(3H, t, J=7.4 Hz), 1.297 (3H, t, J=7.4 Hz), 1.799(3H, s), 2.141(1H, dd, J=5.0, 14.5 Hz), 2.256(3H, s), 2.532(2H, q, J=7.4 Hz), 2.553(2H, q, J=7.4 Hz), 2.869(3H, s), 3.971(1H, dd, J=7.5, 14.5 Hz), 3.992(2H, s), 4.005 (3H, s), 4.021(2H, s), 5.416(1H, dd, J=17.5 Hz), 5.459(1H, d, J=17.4 Hz), 6.989(1H, dd, J=5.1, 7.4 Hz), 7.509–7.963 (5H, m), 9.134(1H, d, J=1.2 Hz)

FAB-MS (m/z): 700 (M+1)$^+$

Compound (H)

$_1$H-NMR (CDCl$_3$) δ (ppm): 1.294 (3H, t, J=7.4 Hz), 1.799(3H, s), 2.149(1H, dd, J=5.0, 14.6 Hz), 2.273(3H, s), 2.533(2H, q, J=7.4 Hz), 2.813 (3H, s), 3.972(1H, dd, J=7.4, 14.6 Hz), 4.008(3H, s), 4.015(2H, s), 4.951 (2H, s), 5.377(1H, d, J=17.4 Hz), 5.418 (1H, d, J=17.4 Hz), 6.973(1H, dd, J=5.0, 7.5 Hz), 7.481–8.037 (5H, m), 9.093(1H, d, J=1.2 Hz)

FAB-MS (m/z): 656 (M+1)$^+$

Substantially the same procedure as in Example 17 was repeated using 34 mg of Compound (G) to give 18.7 mg of Compound II-51.

$^1$H-NMR (CDCl$_3$) δ (ppm): 1.300(3H, t, J=7.4 Hz), 1.325(3H, t, J=7.4 Hz), 2.185(3H, s), 2.514(1H, dd, J=4.8, 14.5 Hz), 2.540(2H, q, J=7.4 Hz), 2.555(2H, q, J=7.4 Hz), 3.384(1H, dd, J=7.5, 14.5 Hz), 3.941(2H, s), 3.976(2H, s), 4.094(3H, s), 4.836(1H, d, J=16.4 Hz), 4.910(1H, d, J=16.3

Hz), 5.781 (1H, s), 6.845 (1H, dd, J=4.8, 7.5 Hz), 7.371–7.843(5H, m), 8.998(1H, s)

FAB-MS (m/z): 616 (M+1)$^+$

Substantially the same procedure as in Example 17 was repeated using 30 mg of Compound (H) to give 20.4 mg of Compound II-56.

$^1$H-NMR (CDCl$_3$) δ (ppm): 1.280(3H, t, J=7.4 Hz), 2.144(3H, s), 2.391(1H, dd, J=4.9, 14.5 Hz), 2.517(2H, q,J=7.4 Hz), 3.320(1H, dd, J=7.4, 14.5 Hz), 3.885(2H, s), 4.069(3H, s), 4.521(1H, d, J=16.3 Hz), 4.631(1H, d, J=16.7 Hz), 4.804(2H, s), 5.769(1H, s), 6.830(1H, dd, J=4.8, 7.4 Hz), 7.375–7.771(5H, m), 8.934(1H, s)

FAB-MS (m/z): 572 (M+1)$^+$

EXAMPLE 19

Compound IV-2

Compound (J) (Japanese Published Unexamined Patent Application No. 120388/87; hereby incorporated by reference) (50 mg, 0.09 mmol) was dissolved in a mixture of 0.5 ml of trifluoroacetic acid and 50 μl of 3N HCl, and the solution was stirred at room temperature for 2 days. The precipitates were collected by filtration and subjected to high performance liquid chromatography (Unisil $_5$C$_{18}$; methanol/water=8/2) to give 8.4 mg of Compound (IV-2).

$^1$H-NMR (DMSO-d$_6$) δ (ppm): 4.947 (2H, s), 7.300–8.010 (6H, m), 8.249(1H, s), 9.266(1H, d, J=2.0 Hz)

FAB-MS (m/z): 390 (M+1)$^+$

EXAMPLE 20

Figure 20:
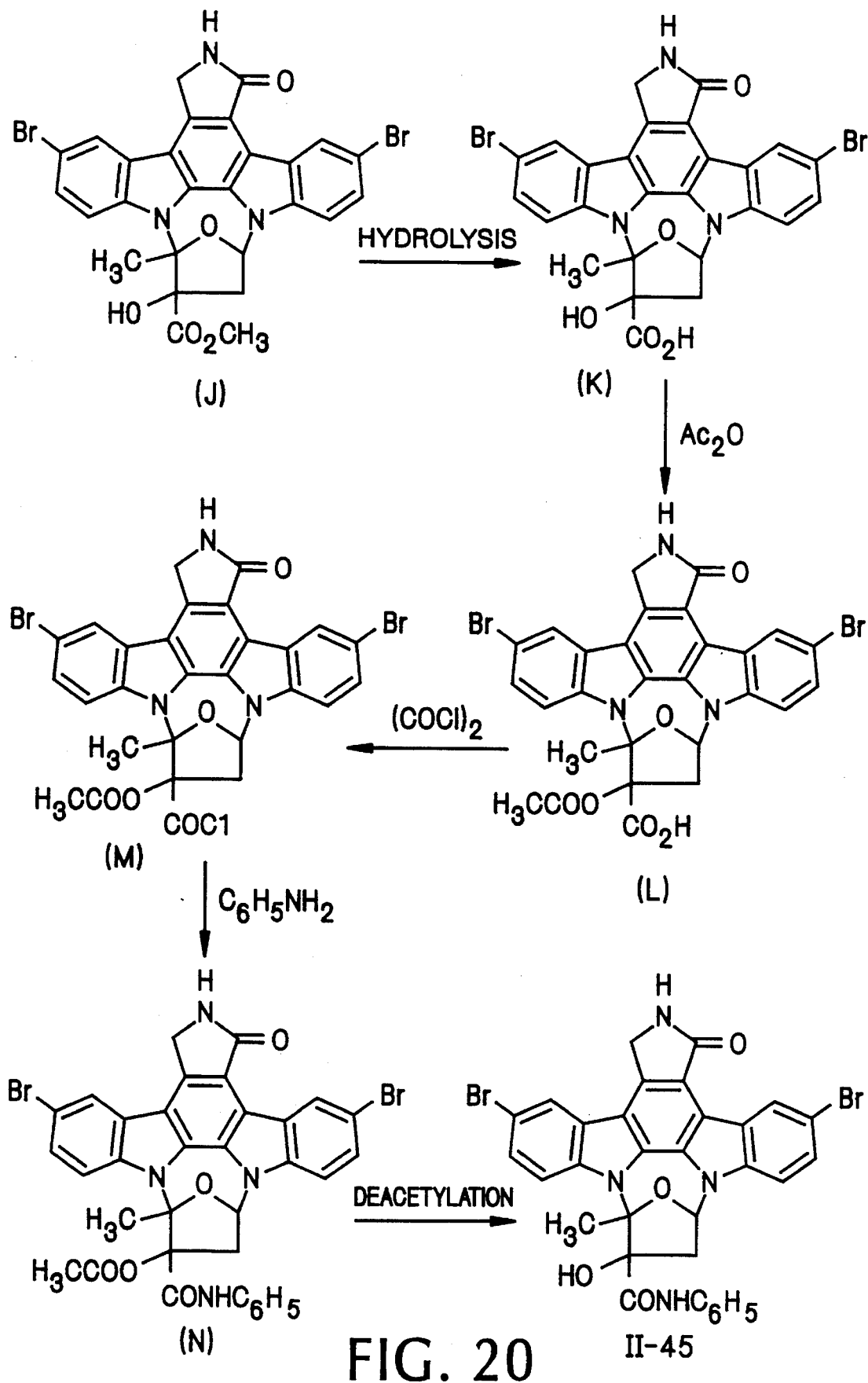
FIG. 20 shows the synthesis of Compound II-45 from starting Compound J.

Compound II-45 can be prepared by the reaction steps shown in FIG. 20. The starting Compound (J) is disclosed in Japanese Published Unexamined Patent Application No. 120388/87 (hereby incorporated by reference).

Compound II-45

Compound (J) (200 mg) was dissolved in 1 ml of dimethylformamide, and then 0.25 ml of an aqueous solution of 23.5 mg of sodium hydroxide was added thereto, followed by stirring at room temperature of 4 hours. After 1N hydrochloric acid was added to adjust the pH of the solution to 1–2, the precipitates were collected by filtration to give 178 mg (yield 91%) of Compound (K).

$^1$H-NMR (DMSO-d$_6$) δ (ppm): 1.965(1H, dd, J=4.8, 14.0 Hz), 2.184(3H, s), 3.364(1H, dd, J=7.5, 14.0 Hz), 5.029 (1H, d, J=18.1 Hz), 5.071(1H, d, J=18.0 Hz), 7.133 (1H, dd, J=4.9, 7.5 Hz), 7.595–8.189(5H, m), 8,733 (1H, s), 9.398(1H, d, J=2.1 Hz)

Compound (K) (168 mg), was dissolved in 3 ml of pyridine, and then 0.44 ml (4.7 mmol) of acetic anhydride was added thereto, followed by stirring at room temperature for 4 days. After evaporation of the solvent, 4 ml of 1N hydrochloric acid was added to the residue, and the precipitates were collected by filtration to give 182 mg (yield quantitative) of Compound (L).

$^1$H-NMR (DMSO-d$_6$) δ (ppm): 1.684(3H, s), 2.135(1H, dd, J=4.9, 14.4 Hz), 2.252(3H, s), 3.865(1H, dd, J=7.6, 14.5 Hz), 5.063(2H, s), 7.255(1H, dd, J=4.9, 7.5 Hz), 7.612–8.582(5H, m), 8.760(1H, s), 9.389(1H, d, J=2.1 Hz)

Compound (L) (172 mg) was suspended in thionyl chloride, followed by stirring at 90° C. for 4.5 hours. After evaporation of the solvent, diethyl ether was added to the residue and the precipitates were collected by filtration to give 180 mg of Compound (M).

Compound (M) (67 mg, 0.1 mmol) was dissolved in 2 ml of ethylene dichloride, and then 180 μl of aniline in tetrahydrofuran was added thereto under ice cooling, followed by stirring at the same temperature for 1 hour. After evaporation of the solvent, the residue was dissolved in a mixture of 2 ml of tetrahydrofuran and 0.5 ml of methanol, and then 1 ml of 1N NaOH was added thereto, followed by stirring at room temperature for 3 hours. To the solution was added 1N hydrochloric acid (1.2 ml) for neutralization, followed by dilution with tetrahydrofuran. The mixture was washed with a saline solution and dried over sodium sulfate. After evaporation of the solvent, the residue was subjected to silica gel column chromatography (chloroform/methanol=98/2) to give Compound II-45 (13 mg from 56 mg of isolated Compound N).

$^1$H-NMR (DMSO-d$_6$) δ (ppm): 2.110 (1H, dd, J=4.9, 13.9 Hz), 2.175(3H, s), 5.019(1H, d, J=18.1 Hz), 5.088(1H, d, J=18.0 Hz), 6.887 (1H, s), 7.119–8.201(11H, m), 8.711 (1H, s), 9.391(1H, d, J=2.2 Hz), 10.071(1H, s)

FAB-MS (m/z): 687 (M+1)$^+$

Other embodiments are within the following claims.
What is claimed is:
1. A compound of the formula (II-4)

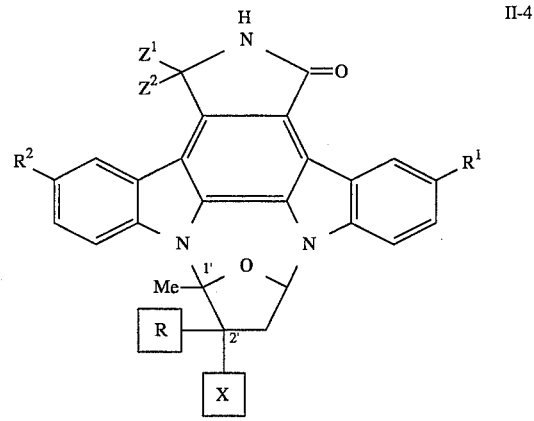

wherein R$^1$, R$^2$, Z$^1$ and Z$^2$ are each H, X is CH$_2$OH, and R is OCH$_3$.

2. A compound of the formula (II-38):

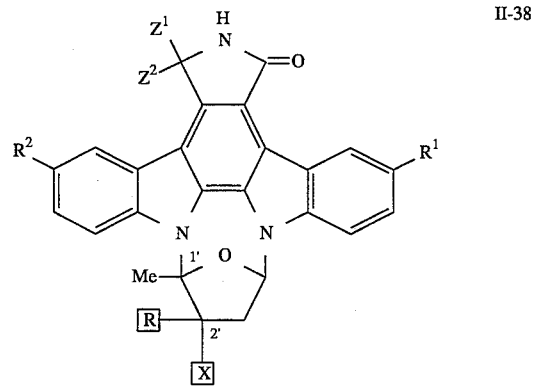

wherein R$^1$, R$^2$, Z$^1$ and Z$^2$ are each H, R is OH, and X is CH$_2$NHCO$_2$C$_6$H$_5$.

3. A compound of the formula (II-45):
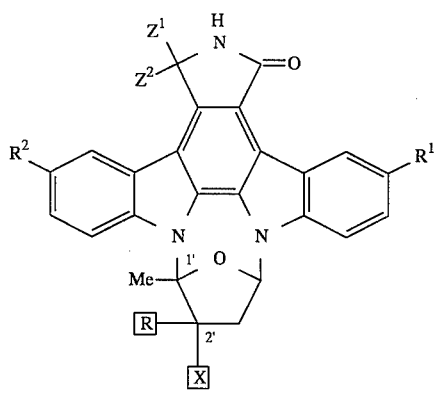
II-45
wherein $R^1$ and $R^2$ are each Br, R is OH, $Z^1$ and $Z^2$ are each H, and X is $CONHC_6H_5$.
4. A compound of the formula (II-57):
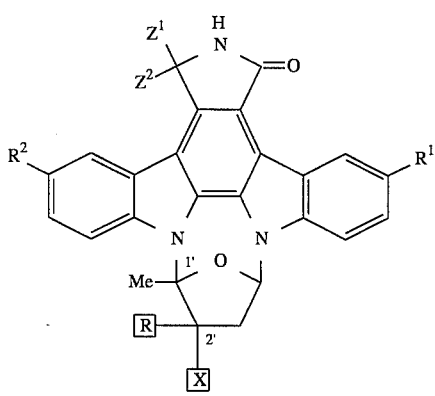
II-57
wherein $R^1$, $R^2$, $Z^1$, and $Z^2$ are each H, R is OH, and X is $CH_2NHCO_2CH_3$.
* * * * *